US008452417B2

(12) United States Patent
Navarro

(10) Patent No.: US 8,452,417 B2
(45) Date of Patent: May 28, 2013

(54) SYSTEM AND METHOD FOR TREATING PAIN WITH PERIPHERAL AND SPINAL NEUROMODULATION

(76) Inventor: Rosa M. Navarro, Granger, IN (US)

( * ) Notice: Subject to any disclaimer, the term of this patent is extended or adjusted under 35 U.S.C. 154(b) by 388 days.

(21) Appl. No.: 12/799,113

(22) Filed: Apr. 19, 2010

(65) Prior Publication Data
US 2011/0022114 A1 Jan. 27, 2011

Related U.S. Application Data

(60) Provisional application No. 61/271,612, filed on Jul. 23, 2009, provisional application No. 61/279,888, filed on Oct. 27, 2009.

(51) Int. Cl.
*A61N 1/0551* (2006.01)

(52) U.S. Cl.
USPC .............................. 607/117; 607/46; 607/118

(58) Field of Classification Search
USPC ............................................ 607/46, 117, 118
See application file for complete search history.

(56) References Cited

U.S. PATENT DOCUMENTS

| | | | |
|---|---|---|---|
| 6,083,252 A | 7/2000 | King | |
| 6,505,075 B1 | 1/2003 | Weiner | |
| 6,745,079 B2 | 6/2004 | King | |
| 7,146,224 B2 | 12/2006 | King | |
| 7,231,256 B2 | 6/2007 | Wahlstrand | |
| 7,324,852 B2 | 1/2008 | Barolat | |
| 7,389,147 B2 | 6/2008 | Wahlstrand | |
| 7,519,431 B2 | 4/2009 | King | |
| 7,813,803 B2 | 10/2010 | King | |
| 2002/0198572 A1 | 12/2002 | Weiner | |
| 2003/0078633 A1* | 4/2003 | Firlik et al. | 607/46 |
| 2006/0122678 A1 | 6/2006 | King | |
| 2006/0161235 A1 | 7/2006 | King | |
| 2006/0167525 A1 | 7/2006 | King | |
| 2006/0206166 A1 | 9/2006 | Weiner | |
| 2006/0253182 A1* | 11/2006 | King | 607/117 |
| 2007/0049988 A1* | 3/2007 | Carbunaru et al. | 607/59 |
| 2007/0073353 A1 | 3/2007 | Rooney | |
| 2007/0073356 A1 | 3/2007 | Rooney | |
| 2007/0073357 A1 | 3/2007 | Rooney | |
| 2007/0118196 A1 | 5/2007 | Rooney | |
| 2007/0150034 A1 | 6/2007 | Rooney | |
| 2007/0168008 A1* | 7/2007 | Olsen | 607/117 |

(Continued)

OTHER PUBLICATIONS

Abejon D, Krames E.S., Peripheral nerve stimulation or is it peripheral subcutaneous field stimulation; Neuromodulation, vol. 12-1, Jan. 2009.

(Continued)

*Primary Examiner* — Christopher D Koharski
*Assistant Examiner* — Michael Carey
(74) *Attorney, Agent, or Firm* — Mark P. Bourgeois

(57) ABSTRACT

A system for treating pain uses spinal cord stimulation and peripheral subcutaneous field stimulation separately or in combination. The system includes an implantable device that is configured to deliver several electrical signals. Several electrical leads are connected to the implantable device. The electrical leads are implanted in the patient such that an electrical signal induces a current to flow between a subcutaneous lumbar region of the patient and a spinal cord region of the patient. The system can also include electrical leads that are implanted in the patient such that an electrical signal induces a current to flow across a lumbar region of the patient. A method for treating leg and back pain is also disclosed.

20 Claims, 20 Drawing Sheets

U.S. PATENT DOCUMENTS

| | | | |
|---|---|---|---|
| 2007/0203542 A1 | 8/2007 | Wahlstrand | |
| 2007/0203544 A1 | 8/2007 | Wahlstrand | |
| 2007/0203546 A1 | 8/2007 | Wahlstrand | |
| 2007/0225765 A1 | 9/2007 | King | |
| 2008/0004675 A1 | 1/2008 | King | |
| 2008/0058878 A1 | 3/2008 | King | |
| 2008/0132970 A1 | 6/2008 | Barolat | |
| 2008/0183224 A1 | 7/2008 | Barolat | |
| 2008/0188906 A1 | 8/2008 | Barolat | |
| 2009/0099439 A1 | 4/2009 | Barolat | |
| 2010/0114204 A1* | 5/2010 | Burnes et al. | 607/4 |

OTHER PUBLICATIONS

Barolat G, Oakley J, Law J, North R, Ketcik B, Sharan A, Epidural spinal cord stimulation with a multiple paddle lead; Neuromodulation Apr. 2001; vol. 4-2 pp. 59-66.

Sharan A, Cameron T, Barolat G, Evolving patterns of spinal cord stimulation in patients implanted for intractable low back; Neuromodulation Jul. 2002; vol. 5-3 p. 167-169.

North R, Kidd D, Olin L, Sieracki F, Petrucci L, Spinal cord stimulation of axial low back pain a prospective controlled; Neuromodulation Jan. 2006; vol. 9-1 pp. 56-67.

Bernstein C, Paicius R, Barkow S, Lempert C, spinal cord stimulation in conjunction with peripheral nerve field stimulation; Neuromodulation 2008; vol. 11-2 pp. 116-123.

Barolat G, Massaro F, He J, Zeme S, Ketcik B, Mapping of sensory responses to epidural stimulation of the intraspinal neural; J. Neurosurgery 1993 78, pp. 233-239.

Krutsch J, McCeney M, Barolat G, et al. A case report of subcutaneous peripheral nerve stimulation for the treatment of; Neuromodulation 2008; vol. 11-2 pp. 112-115.

Mironer Y, Brown C, et al. A new technique of midline anchoring in spinal cord stimulation dramatically reduces lead migration; Neuromodulation 2004; vol. 7-1 pp. 32-37.

Paicius R, Bernstein C, Lempert C, Peripheral nerve field stimulation for the treatment of chronic low back pain preliminary; Neuromodulation 2007; vol. 10-3 pp. 279-290.

Slavin K, Peripheral nerve field stimulation for neuropathic pain; Neurotherapeutics Jan. 2008, vol. 5 pp. 100-106.

* cited by examiner

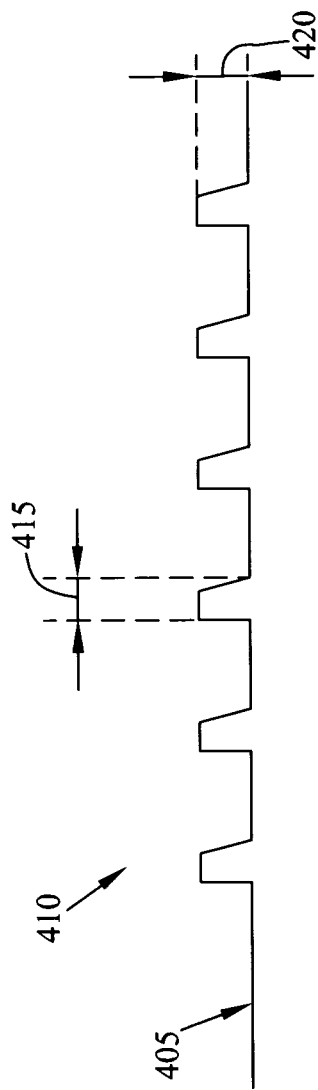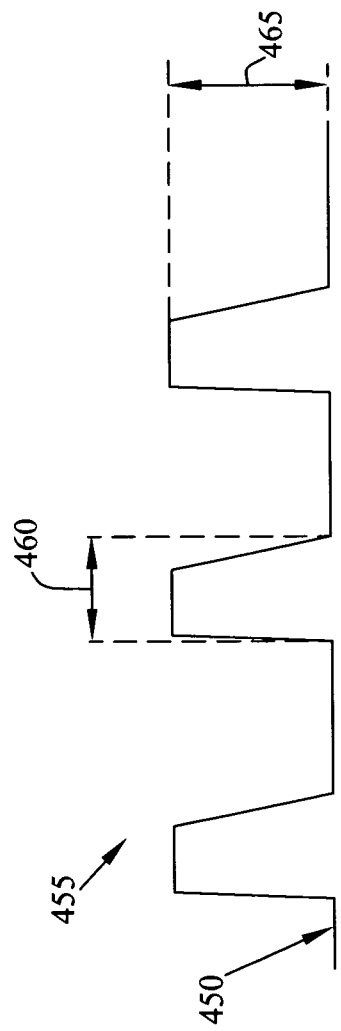

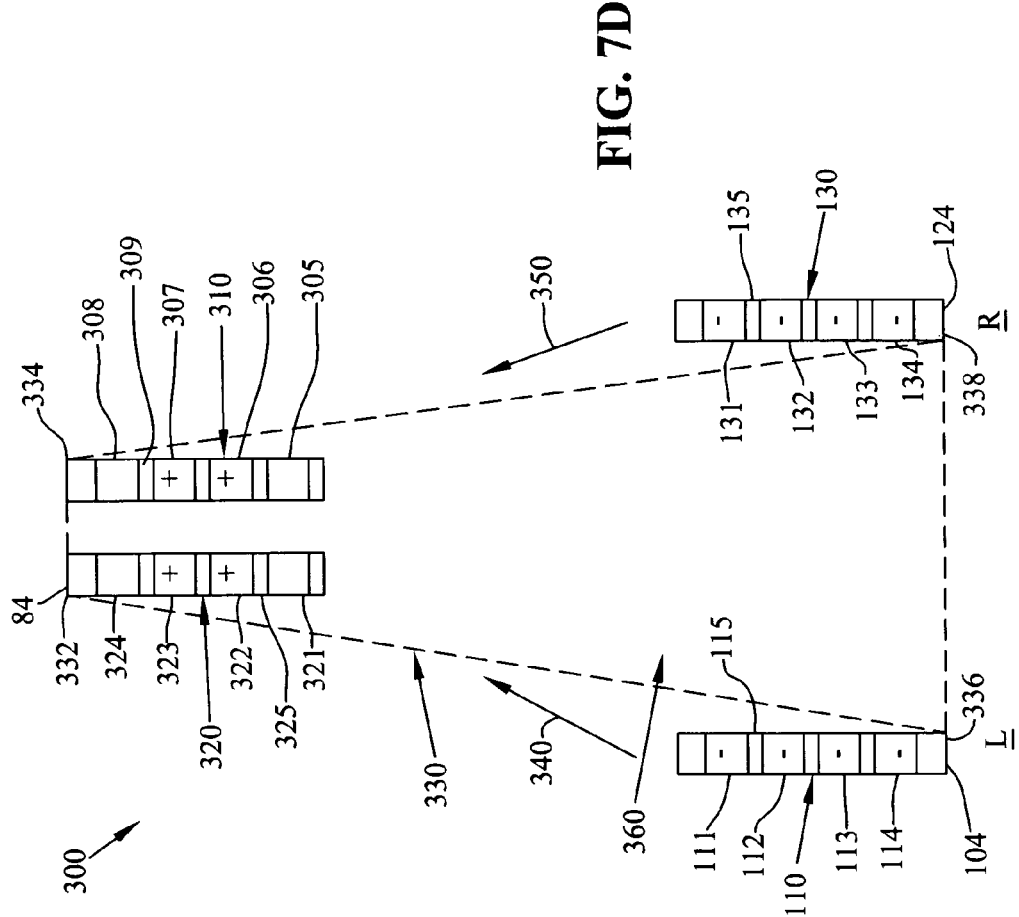

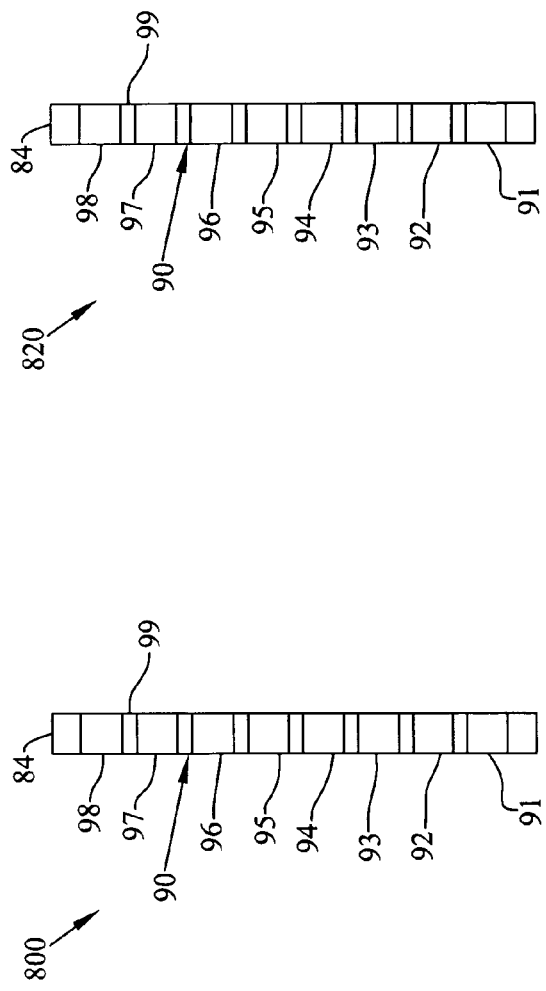
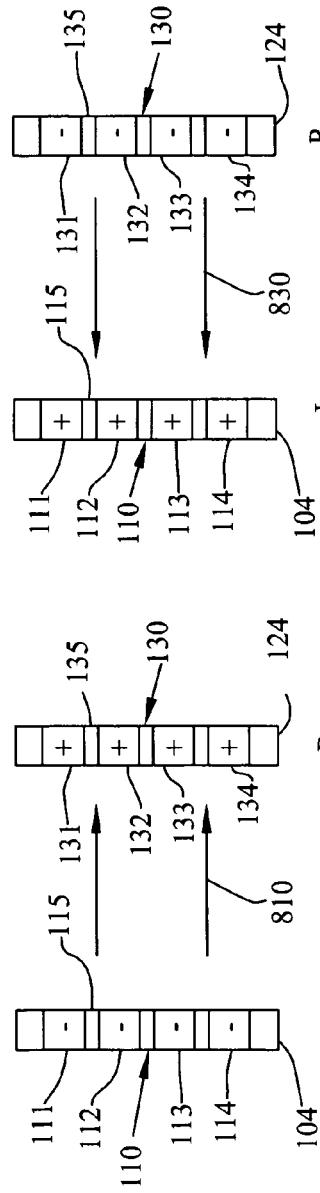
FIG. 8A
FIG. 8B

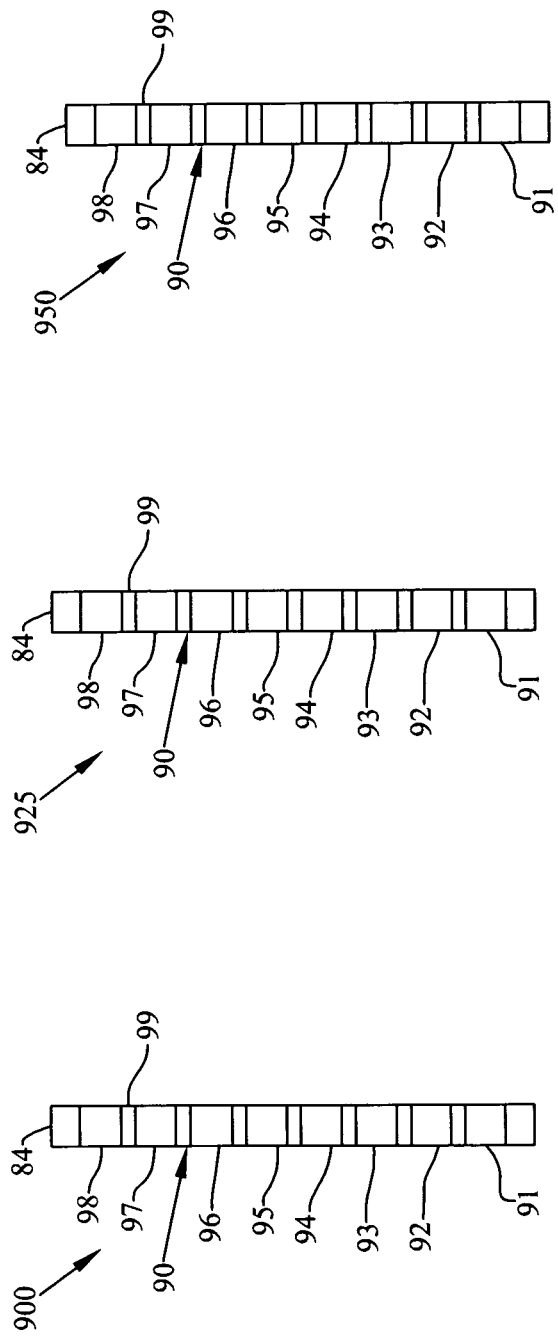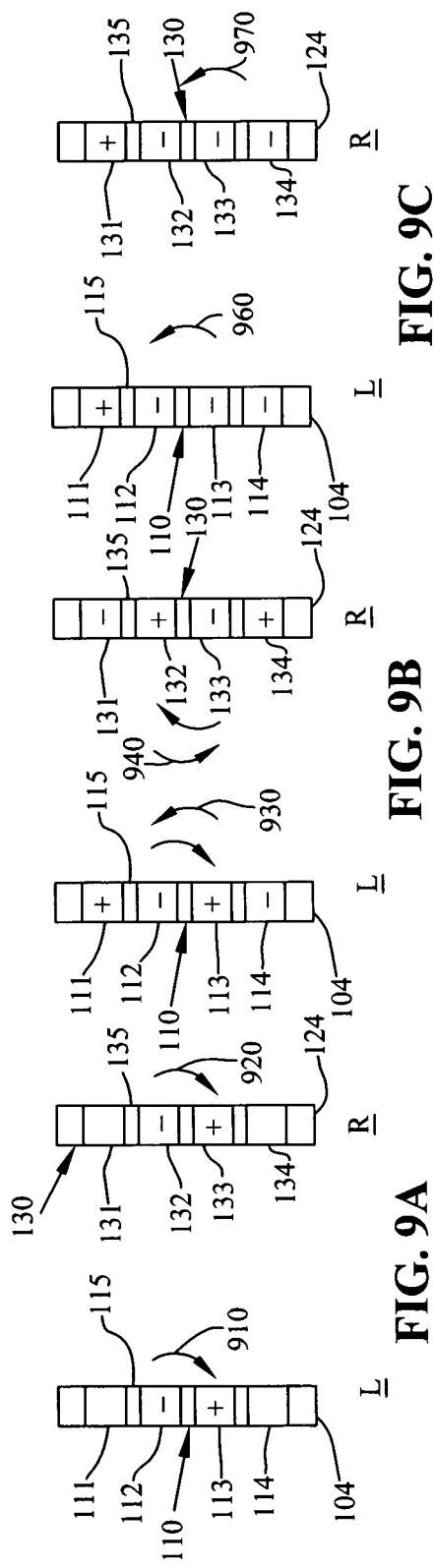
FIG. 9A  FIG. 9B  FIG. 9C

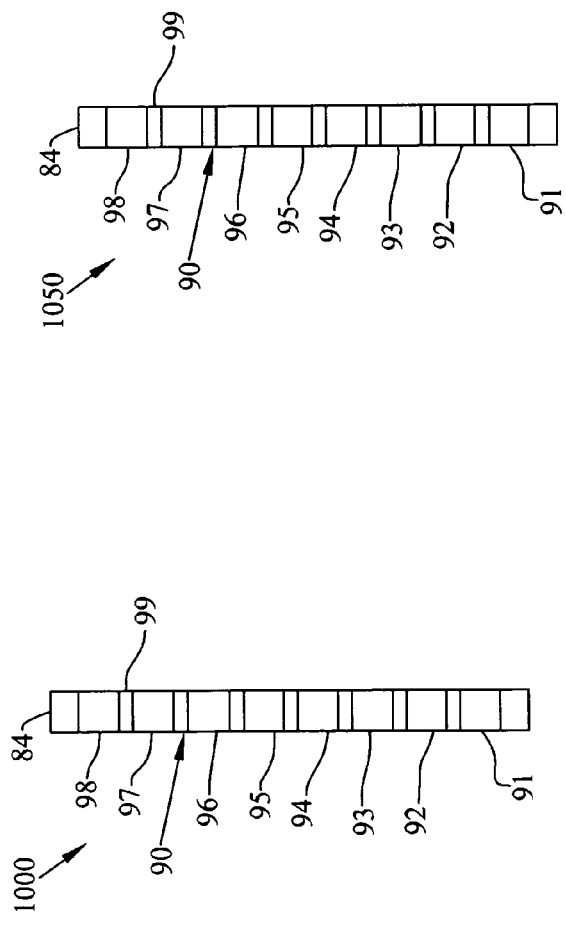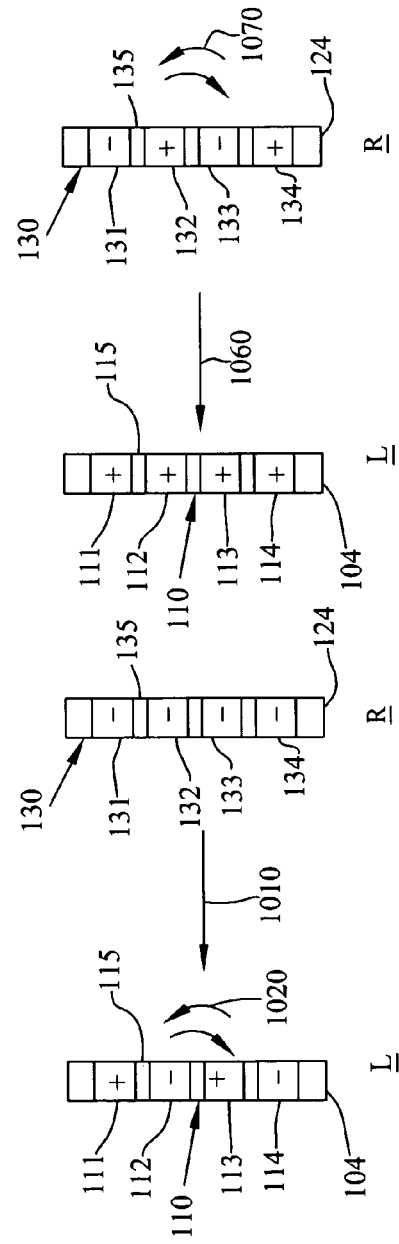
FIG. 10A
FIG. 10B

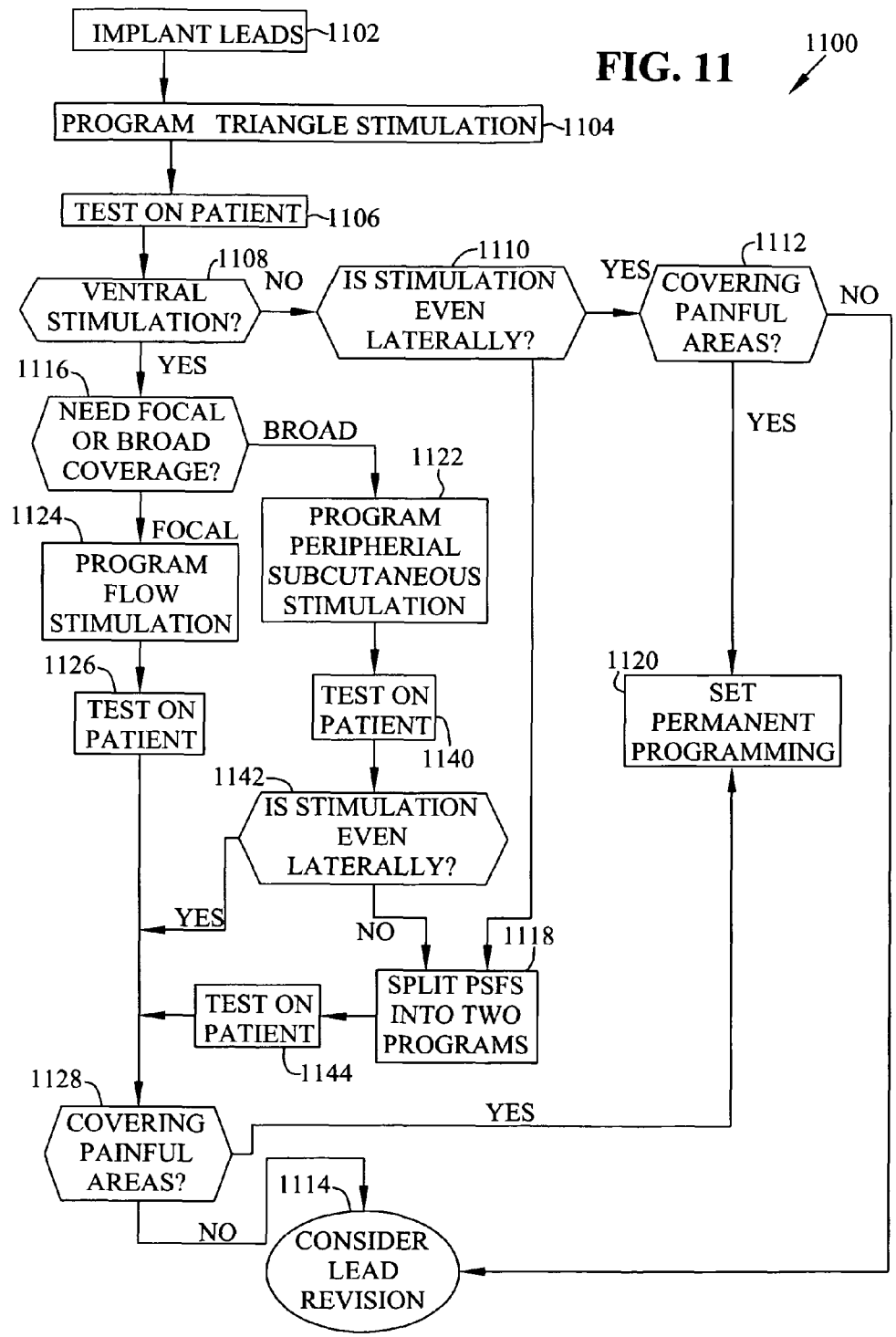

SYSTEM AND METHOD FOR TREATING PAIN WITH PERIPHERAL AND SPINAL NEUROMODULATION

CROSS REFERENCE TO RELATED AND CO-PENDING APPLICATIONS

This application claims priority to U.S. provisional patent application Ser. No. 61/271,612, filed Jul. 23, 2009 entitled, "System and Method for Treating Leg and Back Pain", and U.S. provisional patent application Ser. No. 61/279,888, filed Oct. 27, 2009 entitled, "System and Method for Treating Pain With Peripheral and Spinal Neuromodulation". The entire contents of which are herein incorporated by reference.

FIELD

This application relates to systems and methods for treating pain in patients. More specifically, the present invention uses peripheral and spinal neuromodulation to treat pain.

BACKGROUND

Neurostimulation or neuromodulation devices generate electrical pulses that are connected to electrical leads placed in a patient. The leads deliver electrical signals to nerve tissue to treat a variety of conditions. Spinal cord stimulation (SCS) is an example of neurostimulation in which electrical signals are delivered about the spinal cord for the purpose of pain control. The application of an electrical field to spinal nerves including the spinal cord and spinal nerve roots can block or mask certain types of pain transmitted from regions of the body that are innervated by the stimulated nerve tissue.

The application of an electrical signal to areas of the spinal cord associated with regions of the body afflicted with chronic pain can induce "parathesia", which is a sensation of numbness or tingling in the painful regions. Parathesia can effectively block the transmission of pain sensations to the brain.

Devices for the delivery of neurostimulation typically include an implantable electrical signal generator and one or more electrical leads. The electrical signal generator generates a series of electrical pulses. The electrical signal generator is typically implanted within a pocket created under the skin. Electrical leads are used to conduct the electrical pulses from the implant site of the electrical signal generator to the spinal cord. The electrical leads include an insulative cover with enclosed metal wire conductors that extend through the insulative cover. One end of the electrical lead is connected to the electrical signal generator. Electrodes are located on another end of the electrical lead. The electrodes are placed near the spinal cord.

SCS can work well for leg and lower extremity pain. However, SCS is not reliably effective in treating axial back pain and lower back pain. Chronic lower back pain can be difficult to treat. The ideal treatment is effective, safe and minimally invasive, provides a large reduction in pain, improves the life of the patient and allows the patient to quickly return to normal activities.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In an embodiment, a system for treating pain in a patient can include an implantable device that is configured to generate a plurality of electrical signals. A first set of one or more electrodes is in communication with the implantable device and is implanted proximate to a spinal cord of the patient. A second set of one or more electrodes is in communication with the implantable device and is implanted at least partially within subcutaneous tissue proximate to a lumbar region of the patient and a third set of one or more electrodes is in communication with the implantable device and is implanted at least partially within subcutaneous tissue proximate to the lumbar region of the patient.

In another embodiment, the present invention provides a method of treating pain of a patient. The method includes generating an electrical signal and applying the first electrical signal to the patient such that the electrical signal is induced to flow from a lumbar region of the patient to a thoracic region of the patient.

In an additional embodiment, a system for treating pain in a patient can include a first set of one or more electrodes that are implanted proximate to a spinal cord of the patient to deliver spinal cord stimulation. A second set of one or more electrodes are implanted at least partially within tissue proximate to a lumbar region of the patient to deliver peripheral subcutaneous field stimulation. An implantable device is in communication with the first and second set of electrodes. The implantable device is configured to generate at least one electrical signal that is conveyed between the first and second set of electrodes.

In one other additional embodiment, the present invention is an apparatus for treating pain in a patient. The apparatus includes a first set of electrodes that are implanted proximate to a spinal cord of the patient to deliver spinal cord stimulation. A second set of electrodes are implanted at least partially within tissue proximate to a lumbar region of the patient to deliver peripheral subcutaneous field stimulation. An implantable device is in communication with the first and second set of electrodes. The implantable device has a processor and a memory. Software is operable on the processor to receive instructions, generate at least one electrical signal and supply the electrical signal to the first and second set of electrodes.

In yet another embodiment, the present invention provides a method of treating pain of a patient. The method includes generating an electrical signal and applying the electrical signal to the patient in subcutaneous tissue in a lumbar area. The electrical signal is induced to flow laterally across a spinal axis thereby producing peripheral subcutaneous field stimulation.

In one more embodiment, an apparatus for treating pain in a patient comprises a spinal lead implanted in an epidural space proximate to a spinal cord of the patient to deliver spinal cord stimulation. A pair of subcutaneous leads are implanted in subcutaneous tissue on opposing sides of the spinal cord proximate to a lumbar region of the patient to deliver peripheral subcutaneous field stimulation. At least one implantable device is in communication with the spinal lead and the subcutaneous leads. The implantable device is configured to generate at least one electrical signal that is conveyed between the subcutaneous leads and the spinal lead.

In another embodiment, an apparatus for treating pain in a patient includes an implantable device that is configured to deliver several electrical signals. Several electrical leads are connected to the implantable device. The electrical leads are configured to be implanted in the patient such that at least one of the electrical signals induces a current to flow between a subcutaneous lumbar region of the patient and a spinal cord region of the patient.

In an additional embodiment, the present invention provides a method of treating pain of a patient. The method includes implanting at least one electrical lead. A triangular stimulation program is tested on the patient. If the triangular stimulation program is acceptable to the patient, the triangular stimulation program is stored in an implantable device. If the triangular stimulation program is not acceptable to the patient, a flow stimulation program is tested on the patient. If the flow stimulation program is acceptable to the patient, the flow stimulation program is stored in the implantable device.

BRIEF DESCRIPTION OF THE DRAWINGS

Embodiments are illustrated by way of example and not limitation in the figures of the accompanying drawings, in which like references indicate similar elements and in which:

FIG. 4A is a diagram of electrical signals produced by the implanted device of FIG. 2 in an embodiment;

FIG. 4B is a diagram of electrical signals produced by the implanted device of FIG. 2 in another embodiment;

FIG. 7D is another diagram of electrode polarities representing quadrilateral stimulation for treating low back pain;

FIG. 8A is a diagram of electrode polarities representing flow stimulation for treating low back pain;

FIG. 8B is another diagram of electrode polarities representing flow stimulation for treating low back pain;

FIG. 9A is a diagram of electrode polarities representing peripheral subcutaneous field stimulation;

FIG. 9B is another diagram of electrode polarities representing peripheral subcutaneous field stimulation;

FIG. 9C is an additional diagram of electrode polarities representing peripheral subcutaneous field stimulation;

FIG. 10A is a diagram of electrode polarities representing peripheral subcutaneous field flow stimulation;

FIG. 10B is another diagram of electrode polarities representing peripheral subcutaneous field flow stimulation;

FIG. 11 is a flow chart of a method of treating pain in a patient according to an example embodiment of the present invention;

DETAILED DESCRIPTION

Example apparatuses, methods and systems are described. In the following description, for purposes of explanation, numerous specific details are set forth in order to provide a thorough understanding of example embodiments. It will be evident, however, to one skilled in the art that the present invention may be practiced without these specific details.

Figure 1:
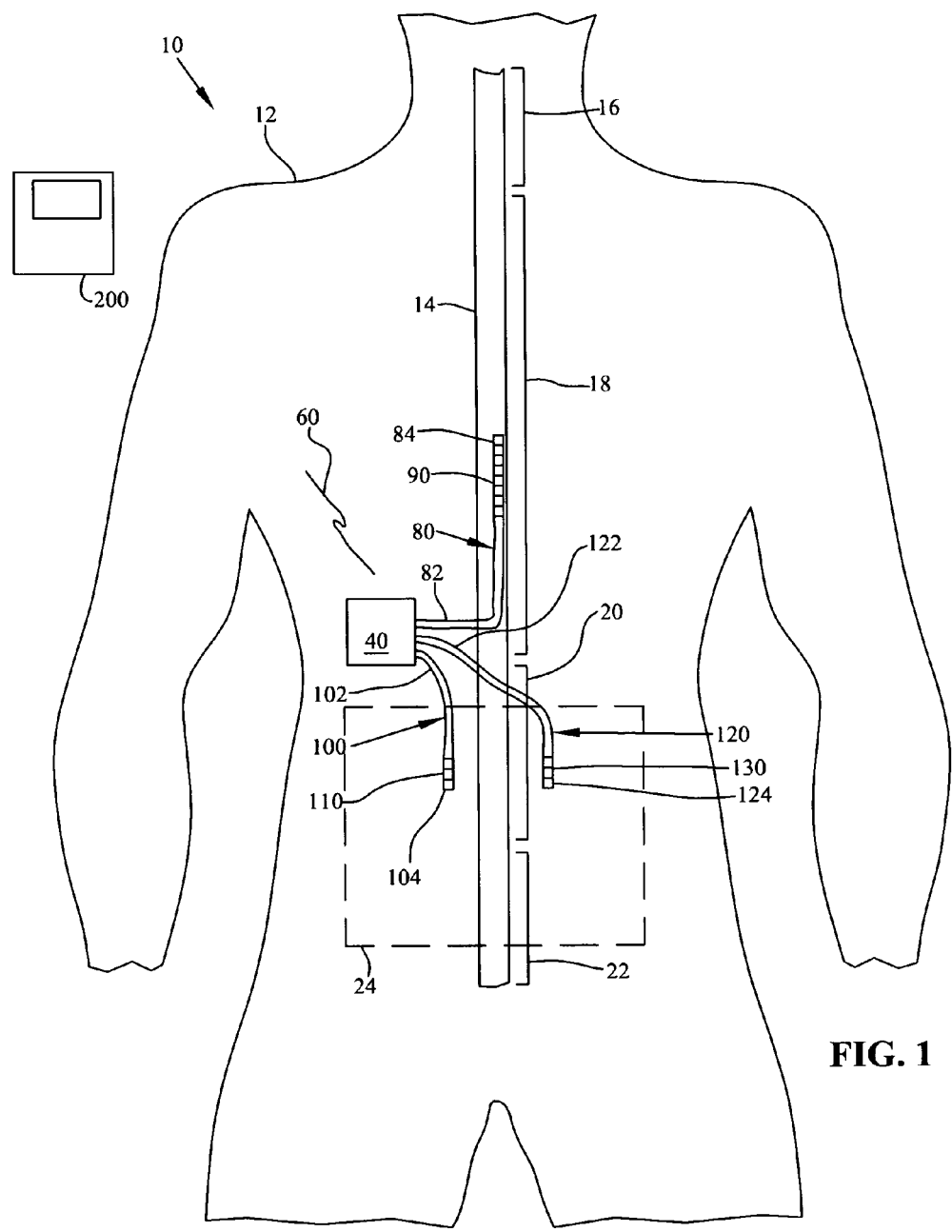
FIG. 1 is a diagram of a system for providing spinal cord stimulation and peripheral subcutaneous field stimulation according to an example embodiment of the present invention.

FIG. 1 illustrates an example apparatus or system 10 for treating leg and back pain. A patient 12 can have a wide variety of painful conditions that are treated by system 10. In FIG. 1, the view of patient 12 is a posterior view or looking toward the back of the patient. Patient 12 may suffer from low back pain, leg pain, failed back syndrome or low back syndrome or failed back, radicular pain syndrome, radiculopathies, herniated disks, postlaminectomy pain, unsuccessful disk surgery, degenerative disk disease, epidural fibrosis, arachnoiditis, complex regional pain syndrome, occipital neuralgia, occipital headache, neck pain, arm pain, intercostal neuralgia, degenerative scoliosis, kyphosis, peripheral nerve damage and various other neuralgias.

Patient 12 can have a spinal cord 14 with several sections. Spinal cord 14 has a cervical section 16, a thoracic section 18, a lumbar section 20 and a sacral section 22. Various nerve roots (not shown) extend laterally outwardly form each side of spinal cord 14 through the epidural space (not shown). Patient 12 may have a lumbar-sacral area or region 24 about which the patient experiences one or more types of pain. For example, patient 12 may experience low back pain in region 24.

System 10 can include an implantable device 40, programming device 200 and electrical leads 80, 100 and 120. Implantable device 40 is configured to generate a series of one or more electrical signals that are delivered to the patient through electrical leads 80, 100 and 120. Electrical leads 80, 100 and 120 are connected to implantable device 40. Programming device 200 can instruct implantable device 40 to generate and deliver a series of electrical stimulation signals to patient 12.

Spinal lead 80 has a proxil end 82, a distal end 84 and several electrodes 90 that can be selectively energized. Proxil end 82 can be connected to implantable device 40. Electrical lead 80 can be implanted percutaneously using a needle such that electrodes 90 are proximate or adjacent to spinal cord 14 in a thoracic region 18.

While electrodes 90 is shown placed proximate spinal cord 14 in thoracic section 18. Electrodes 90 could be placed proximate spinal cord 14 in cervical section 16, lumbar section 20 or sacral section 22 to treat painful conditions proximate these sections or to treat painful conditions that are innervated from these sections.

Subcutaneous lead 100 has a proxil end 102, a distal end 104 and several electrodes 110 that can be selectively energized. Proxil end 102 can be connected to implantable device 40. Electrical lead 100 can be implanted in subcutaneous tissue such that electrodes 110 are on one side of spinal cord 14 in lumbar-sacral region 24.

Subcutaneous lead 120 has a proxil end 122, a distal end 124 and several electrodes 130 that can be selectively energized. Proxil end 122 can be connected to implantable device 40. Electrical lead 120 can be implanted in subcutaneous tissue such that electrodes 130 are on another side of spinal cord 14 in lumbar-sacral region 24.

While electrodes 110 and 130 are shown placed proximate lumbar-sacral region 24. Electrodes 110 and 130 could be placed proximate cervical section 16, thoracic section 18 or sacral section 22 to treat painful conditions proximate these sections or to treat painful conditions that are innervated from these sections.

Electrodes 90 can deliver spinal cord stimulation (SCS) to the patient. Electrical signals are delivered about the spinal cord. The application of an electrical signal to spinal nerves including the spinal cord and spinal nerve roots can effectively block or mask certain types of pain transmitted from regions of the body that are innervated by the stimulated nerve tissue. The electrical signal can create an electrical field about electrodes 90 that may be contained about electrodes 90 or may flow to other additional electrodes.

Electrodes 110 and 130 can deliver peripheral subcutaneous field stimulation (PSFS) to the patient. Electrical signals are delivered about and between the regions that electrodes 110 and 130 are placed. Peripheral nerves are nerves in the body other than the nerves of the brain or spinal cord. Peripheral nerve injury can also result in the development of chronic pain. PSFS delivers electrical signals in subcutaneous tissue adjacent to specific nerves to control pain in targeted areas such as lumbar-sacral region 24. The application of an electrical signal to lumbar-sacral region 24 can effectively block or mask certain types of pain transmitted from regions of the body that are innervated by the stimulated nerve tissue. The electrical signal can create an electrical field about electrodes 110 and 130 that may be contained about electrodes 110 and 130 or may flow to other additional electrodes.

The application of an electrical signal to areas of the spinal cord 14 or lumbar-sacral region 24 associated with regions of the body afflicted with chronic pain can induce "parathesia", which is a sensation of numbness or tingling in the painful regions. Parathesia can effectively block the transmission of pain sensations to the brain. Spinal cord stimulation and peripheral subcutaneous field stimulation either alone or in combination can induce paresthesia to block the transmission of pain sensations to the brain.

In one embodiment, system 10 may deliver a triangular stimulation (TS) of electrical signals to patient 12. The electrical signals associated with triangular stimulation travel or communicate between electrodes 110, 130 and electrodes 90.

In another embodiment, system 10 may deliver flow stimulation (FS) of electrical signals to patient 12. The electrical signals associated with flow stimulation travel or communicate laterally between electrodes 110 and 130. In another embodiment, system 10 may deliver peripheral subcutaneous field stimulation (PSFS) of electrical signals to patient 12. The electrical signals associated with PSFS travel or communicate within each electrode 110 and 130. In another embodiment, system 10 may deliver peripheral subcutaneous field flow stimulation (FFS) of electrical signals to patient 12. The electrical signals associated with FFS travel or communicate within one of electrodes 110 or 130 also between electrodes 110 and 130.

Figure 2:
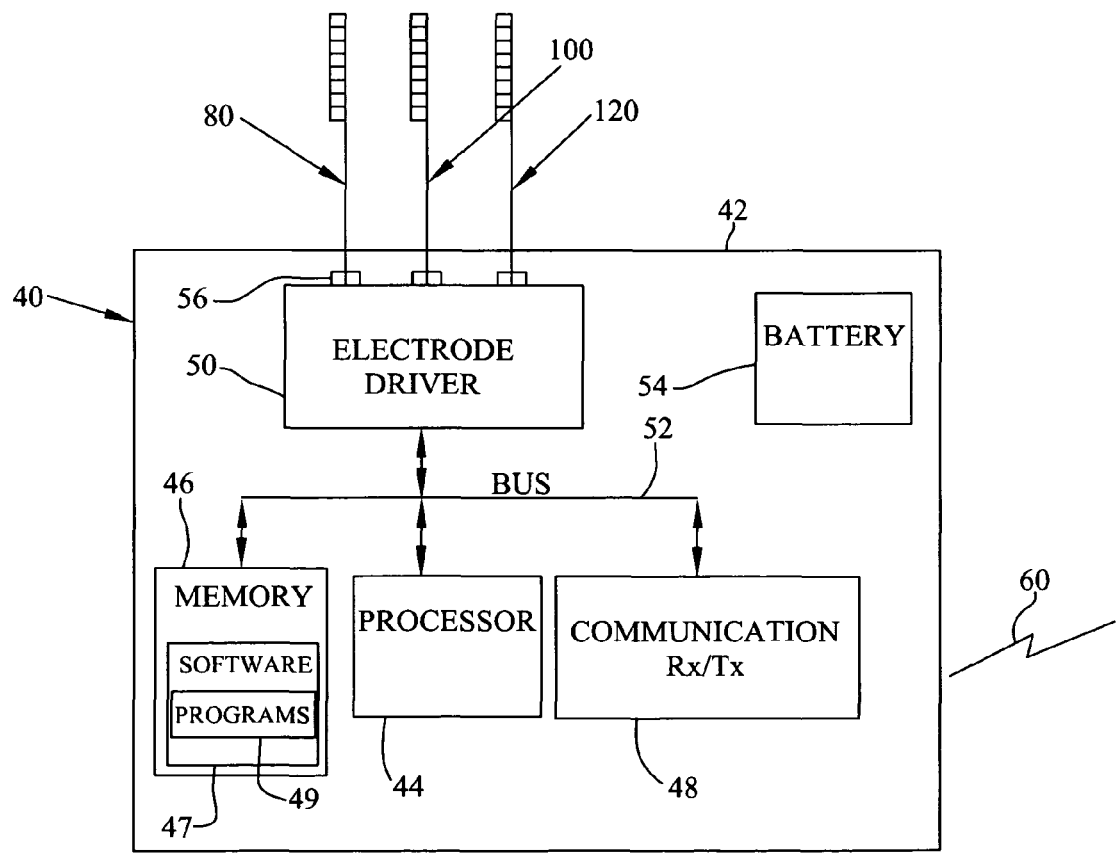
FIG. 2 is a schematic diagram of an implantable device according to an example embodiment of the present invention.

With reference now to FIG. 2, additional details of implantable device 40 will now be described. Implantable device 40 can include an outer housing or case 42 that contains the components of implantable device 40. Housing 42 can be formed from any suitable material that is compatible within the human body such as titanium. Implantable device 40 includes a central processing unit or processor 44, memory 46, communication circuit 48, electrode driver circuit 50, all of which communicate with each other via a communication bus 52. A battery 54 is connected to each of the components in order to supply power to implantable device 40. Battery 54 may be rechargeable or non-rechargeable. Battery 54 may be a lithium ion battery, nickel metal hydride, nickel cadmium or any other suitable type of battery. The components that make up implantable device 40 can be assembled on a hybrid circuit board or printed circuit board (not shown) using conventional electronic assembly techniques.

Communication circuit 48 can communicate with programming device 200 (FIG. 1) through a wireless signal 60. Wireless signal 60 can be a wide variety of electronic signals such as RF, infrared or optical signals. Stimulation programs can be downloaded from programming device 200 through communication circuit 48 to implantable device 40 and can be stored in memory 46.

Patient data can be sent from implantable device 40 through communication circuit 48 to programming device 200. Implantable device 40 can collect data during use by a patient such as the usage of each stimulation program and any error conditions or malfunctions that may occur. The patient data can be collected by a clinician or physician for adjustment of the stimulation programs or for repair of any defects.

Processor 44 can be a microprocessor, a field programmable gate array or an application specific integrated circuit. One or more instructions, instruction sets or software 47 can be stored on a machine-readable medium or memory 46 embodying any one or more of the methodologies or functions described herein. Memory 46 can be a random access memory (RAM), read only memory (ROM), programmable memory (PROM) or any other suitable memory. Software 47 may also reside, completely or at least partially, within any memory contained within processor 44 during execution thereof by the implantable device 40. Software 47 can store stimulation programs 49 that operate on processor 44.

The term "memory or machine-readable medium" shall also be taken to include any medium that is capable of storing, encoding or carrying out a set of instructions for execution by the processor and that cause the processor to perform any one or more of the methodologies shown in the various embodiments of the present invention. Machine-readable medium or memory shall accordingly be taken to include, but not be limited to, solid-state memories, optical and magnetic media, and carrier wave signals.

Stimulation programs 49 may include programs for either TS, FS, SCS, PSFS, FFS or any combination of the foregoing programs. In one embodiment, TS, FS, SCS, PSFS, FFS may be delivered concurrently or in combination to the patient. In another embodiment, TS, FS, SCS, PSFS, FFS may be delivered in an alternating manner to the patient. Stimulation programs 49 can also include information as to when each program runs. Stimulation programs 49 may define a time of day or week for each stimulation program to be run. For example, stimulation program 49 may cause TS to be delivered during nighttime hours and both TS and SCS to be delivered during daytime hours.

Processor 44 controls implantable device 40 to deliver various types of neurostimluation according to one or more of the stimulation programs 49. Processor 44 is communication with electrode driver circuit or module 50. Electrode driver circuit 50 contains output driver circuits that can be impedance matched to electrical leads 80, 100 and 120. Electrode driver circuit 50 generates electrical signals at the proper frequency, amplitude and pulse width for delivery to the patient through electrical leads 80, 100 and 120.

Electrical leads 80, 100 and 120 can be coupled to implantable device using one or more conventional electronic connectors 56. In an embodiment, the electronic connectors are high reliability electronic connectors with strain relief.

Implantable devices 40 are commercially available from Medtronic Corporation of Minneapolis, Minn. and from Saint Jude Medical Corporation of Saint Paul, Minn.

Figure 3:
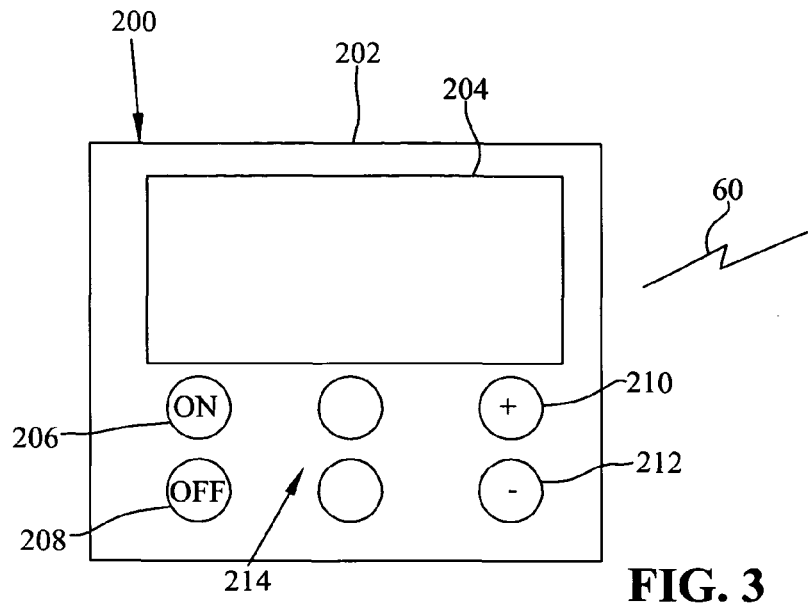
FIG. 3 is a top view of a programming device according to an example embodiment of the present invention.

FIG. 3 illustrates a programming device 200 that can communication stimulation programs and instructions to implantable device 40 through wireless signal 60. Programming device 200 includes a housing 202 and a display 204 such as a LCD, LED or touch screen display. Display 204 can show data and information relating to stimulation programs for TS, FS, SCS, PSFS and FFS. Various buttons and keys are used to at least partially control programming device 200. An on button 206 and off button 208 turn programming device 200 on an off A plus key 210 and a minus key 212 can be used to increase or decrease various parameters of programming device 200. Other keys such as keypad 214 may be used by a user to interact with programming device 200. More or fewer keys may be used. In an embodiment, keypad 214 may be an alphanumeric keypad. Programming device 200 has a receiver and transmitter that can send and receive wireless signals 60 to communication circuit 48 (FIG. 2).

A clinician or physician may use programming device 200 to input stimulation programs for TS, FS, SCS, PSFS and FFS to implantable device 40 (FIG. 2). A clinician or physician can use programming device 200 to select and set various stimulation program parameters such as amplitude, pulse width, pulse rate, electrode polarity, duty cycle and time of delivery for TS, FS, SCS, PSFS and FFS.

Multiple stimulation programs may be configured by programming device 200 and downloaded to implantable device 40. In one embodiment, programming device 200 may be pre-programmed with multiple predefined stimulation programs at the factory. In another embodiment, new stimulation programs may be communicated to programming device 200 through the interne or through the use of another medium during the use of programming device 200.

Programming device 200 may allow a clinician to test various stimulation programs with a wide variety of parameters for TS, FS, SCS, PSFS and FFS in order to maximize the pain relief experienced by the patient. Preferred stimulation programs may be indentified during a test or trial period. Feedback from the patient can be used to select optimal stimulation programs for permanent storage in implantable device 40. Programming devices 200 are commercially available from Medtronic Corporation of Minneapolis, Minn. and from Saint Jude Medical Corporation of Saint Paul, Minn.

As shown in FIG. 4A, an electrical signal or waveform 405 can be generated by implantable device 40 (FIG. 2). Electrical signal or waveform 405 has several parameters that can be set by a clinician or physician using programming device 200 (FIG. 3). Electrical signal 405 can be generated by the implantable device and delivered to the patient. Electrical signal or waveform 405 has a frequency 410, pulse width 415 and amplitude 420. Each of the parameters of frequency 410, pulse width 415 and amplitude 420 can be determined by the clinician or physician and can be input to the implantable device as part of a stimulation program.

In addition, the clinician or physician can determine the length of time that the electrical signal is applied and specific times during the day that various electrical signals are delivered to the patient. In one embodiment, electrical signal 405 may deliver triangular stimulation and may have a frequency 410 of 20 Hertz, a pulse width 415 of 240 micro-seconds and amplitude 420 of 2.2 volts. Other frequencies, pulse widths and amplitudes can be used. Waveform 405 may be applied between electrical leads 100, 120 and 90.

In one embodiment, amplitude 420 may start with a relatively low magnitude and ramp up to maximum amplitude and then ramp back down to a relatively low magnitude. In other embodiments, the frequency 410 or pulse width 415 may be varied by increasing or decreasing during each cycle of stimulation delivered.

With reference to FIG. 4B, an electrical signal or waveform 450 can be generated by implantable device 40 (FIG. 2). Electrical signal or waveform 450 has several parameters that can be set by a clinician or physician using programming device 200 (FIG. 3). Electrical signal 450 can be generated by implantable device 40 and delivered to the patient. Electrical signal or waveform 450 has a frequency 455, pulse width 460 and amplitude 465. Each of the parameters of frequency 455, pulse width 460 and amplitude 465 can be determined by the clinician or physician and can be input to the implantable device as part of a stimulation program.

In addition, the clinician or physician can determine the length of time that the electrical signal is applied and specific times of the day that various electrical signals are delivered to the patient. In one embodiment, electrical signal 450 may deliver spinal cord stimulation and may have a frequency 410 of 20 Hertz, a pulse width 415 of 450 micro-seconds and amplitude 465 of 4.7 volts. Other frequencies, pulse widths and amplitudes can be used. Waveform 450 may be applied to electrical lead 90.

In one embodiment, amplitude 465 may start with a relatively low magnitude and ramp up to maximum amplitude and then ramp back down to a relatively low magnitude. In other embodiments, the frequency 455 or pulse width 460 may be varied by increasing or decreasing during each cycle of stimulation delivered.

Figure 5:
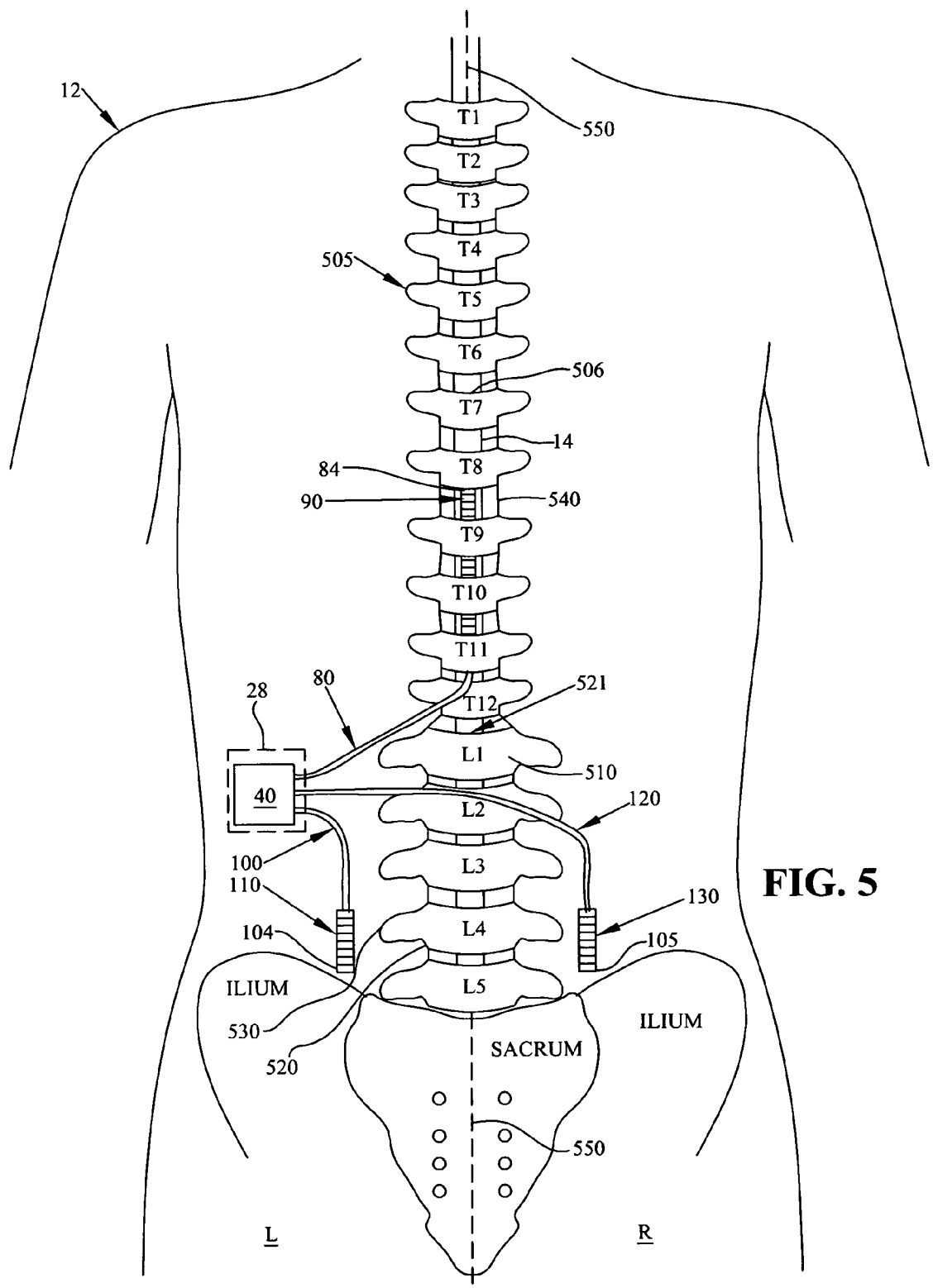
FIG. 5 is a detailed diagram of an electrical lead implanted in an epidural space and pair of subcutaneous electrical leads implanted in subcutaneous tissue in a lumbar region showing the specific anatomical placement of the electrical leads in an embodiment.

FIG. 5 illustrates additional details on the specific anatomical placement of electrical leads in an embodiment. A posterior view of patent 12 is shown in FIG. 5. Patient 12 has a vertebrae column 505 that contains individual vertebrae 510. The vertebrae include the thoracic vertebrae T1, T2, T3, T4, T5, T6, T7, T8, T9, T10, T11 and T12 (T1-T12), the lumbar vertebrae L1, L2, L3, L4 and L5 (L1-L5) and the sacrum. The location of the ilium and iliac crest are also shown. The discs that are located between the vertebrae are omitted in FIG. 5 in order to show additional detail.

Spinal cord 14 extends lengthwise through the vertebrae column 505. Spinal cord 14 can have a midline or spinal axis 550 that is parallel with vertebrae column 505. Axis 550 can divide the body of patient 12 into a left half L and a right half R. Each vertebra has a vertebral foramen 506. The spinal cord 14 extends through each vertebral foramen 506. An epidural space 540 surrounds the spinal cord 14.

Each vertebra T1-T12 and L1-L5 has a pair of lateral pedicels 520 that extend posterior from a body 521 of the vertebrae. A transverse process 530 is connected to each of the pedicels 520 and extends laterally and posterior outward.

Electrical lead 80 is implanted percutaneously within the epidural space 540. Electrical lead 80 can be implanted using a 14 gauge, 6 inch long Touhy needle with local anesthesia. Only the entry site of the needle will have local anesthetic, not the needle tract. Electrical lead 80 is placed such that electrodes 90 are proximate vertebrae T8, T9 and T10 and spinal cord 14. Electrodes 90 can enter the contralateral side to the painful side from a paramedian approach and be located an anterior side of spinal cord 14 within epidural space 540. Electrodes 90 can cross axis 550 at vertebrae T8 or T9. Approximately one half of the lead can be to the left of axis 550 and the other half to the right of axis 550.

The distal end 84 can be located at the tip of vertebrae T8. Electrical lead 80 exits the epidural space 540 between vertebrae T11 and T12 and extends through subcutaneous tissue to implantable device 40. While one electrical lead 80 is shown, more than one electrical lead may be placed proximate spinal cord 14.

Electrical lead 100 is implanted subcutaneously within the subcutaneous tissue. Electrical lead 100 is placed such that electrodes 110 are located approximately 1.5 inches laterally from spinal axis 550. While shown proximate vertebrae L4, L5, electrodes 110 can be located proximate any vertebrae from T12 down to the bottom of the sacrum. Electrodes 110 can be substantially parallel to spinal cord 14 or spinal cord axis 550. The distal end 104 can be located lateral from the transverse process 530 of vertebrae L5. Electrical lead 100 extends through subcutaneous tissue to implantable device 40.

Electrical lead 120 is implanted subcutaneously within the subcutaneous tissue. Electrical lead 120 is placed such that electrodes 130 are located approximately 1.5 inches laterally from spinal axis 550. While shown proximate vertebrae L4 and L5, electrodes 130 can be located proximate any vertebrae from T12 down to the bottom of the sacrum. Electrodes 130 can be substantially parallel to spinal cord 14 or spinal cord axis 550. The distal end 124 can be located lateral from the transverse process 530 of vertebrae L5. Electrical lead 120 extends through subcutaneous tissue across vertebrae column 505 to implantable device 40.

Electrical leads 100 and 120 can be implanted using a 14 gauge, 6 inch long Touhy needle with local anesthesia. Electrical leads 100 and 120 may be anchored to the skin using a twist-lock anchor for an external trial placement and using a titon anchor attached to fascia for permanent placements. Electrodes 110 and 130 may be placed closer to or farther away from the spinal axis 550 or L4/L5 pedicels 520 depending upon the location of pain.

In an embodiment, electrodes 110 and 130 may not be aligned parallel with spinal cord 12 but are aligned with underlying nerves that are desired to be stimulated. For example, electrodes 110 and 130 may be aligned with a illo-hypogastric nerve, a illoinguinal nerve, a genitofemoral nerve, a lateral femoral cutaneous nerve, a femoral nerve, a obturator nerve, a lumbosacral trunk root, a superior gluteal nerve, an inferior gluteal nerve, a common peroneal nerve, a tibial nerve, a posterior cutaneous nerve, a pudendal nerve, a quadratus femoris nerve, a obturator nerve and a gamellus nerve.

Implantable device 40 can be implanted or placed within a subcutaneous pocket 28 that is formed to receive implantable device 40. Subcutaneous pocket 28 can be located in a variety of locations and is usually located away from the location of the electrodes. Subcutaneous pocket can be located in an area such as the buttocks, abdomen or chest.

Electrodes 90, 110 and 130 can be used to deliver triangular stimulation for treating axial back pain. Electrodes 90 can be used to deliver spinal cord stimulation for treating neuropathic pain such as neuropathy or radiculopathy that involves a portion of one or more legs. Electrodes 110 and 130 can be used to deliver flow stimulation, peripheral subcutaneous field stimulation and peripheral subcutaneous field flow stimulation.

Figure 6:
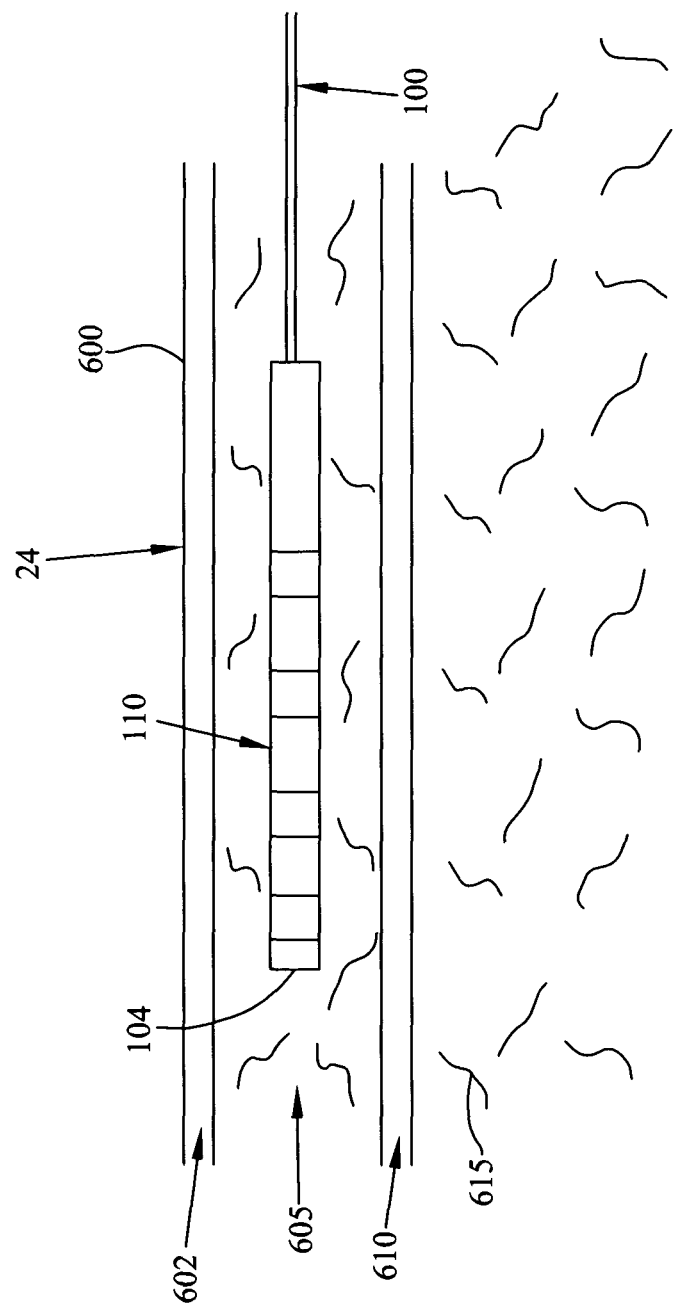
FIG. 6 is a cross-sectional view of a subcutaneous lead implanted in subcutaneous tissue.

Referring to FIG. 6, a subcutaneous electrical lead implanted in subcutaneous tissue of a patient is shown. The patient has an epidermis 600 and dermis 602 located within a painful region 24. Subcutaneous tissue 605 is located below the dermis 602. A network of peripheral nerves or nerve fibers 615 is located within tissue below fascia 610. Electrical lead 100 with electrodes 110 can be surgically placed within subcutaneous tissue 605.

Electrical lead 100 can be placed within subcutaneous tissue 605. In other embodiments, electrical lead 100 may be implanted in the epidermis 600 or the dermis 602. Electrical lead 100 is implanted within subcutaneous tissue 605 using a hollow needle (not shown). The needle may be inserted through the dermis and the epidermis into the subcutaneous tissue 605 within painful region 24. Electrical lead 100 and electrodes 110 can be inserted or threaded through the needle into the proper position within subcutaneous tissue 605. The needle is removed leaving electrical lead 100 and electrodes 110 in place.

Electrodes 110 can be placed approximately one centimeter below the epidermis 600. End 102 (FIG. 1) of electrical lead 100 can be threaded through subcutaneous tissue to the implant site of implantable device 40 (FIG. 1) where is it connected to implantable device 40 using electrical connector 56 (FIG. 2). When an electrical signal is applied to electrodes 110, various types of stimulation can be delivered to the patient proximate painful region 24.

Figures 7A, 7B:
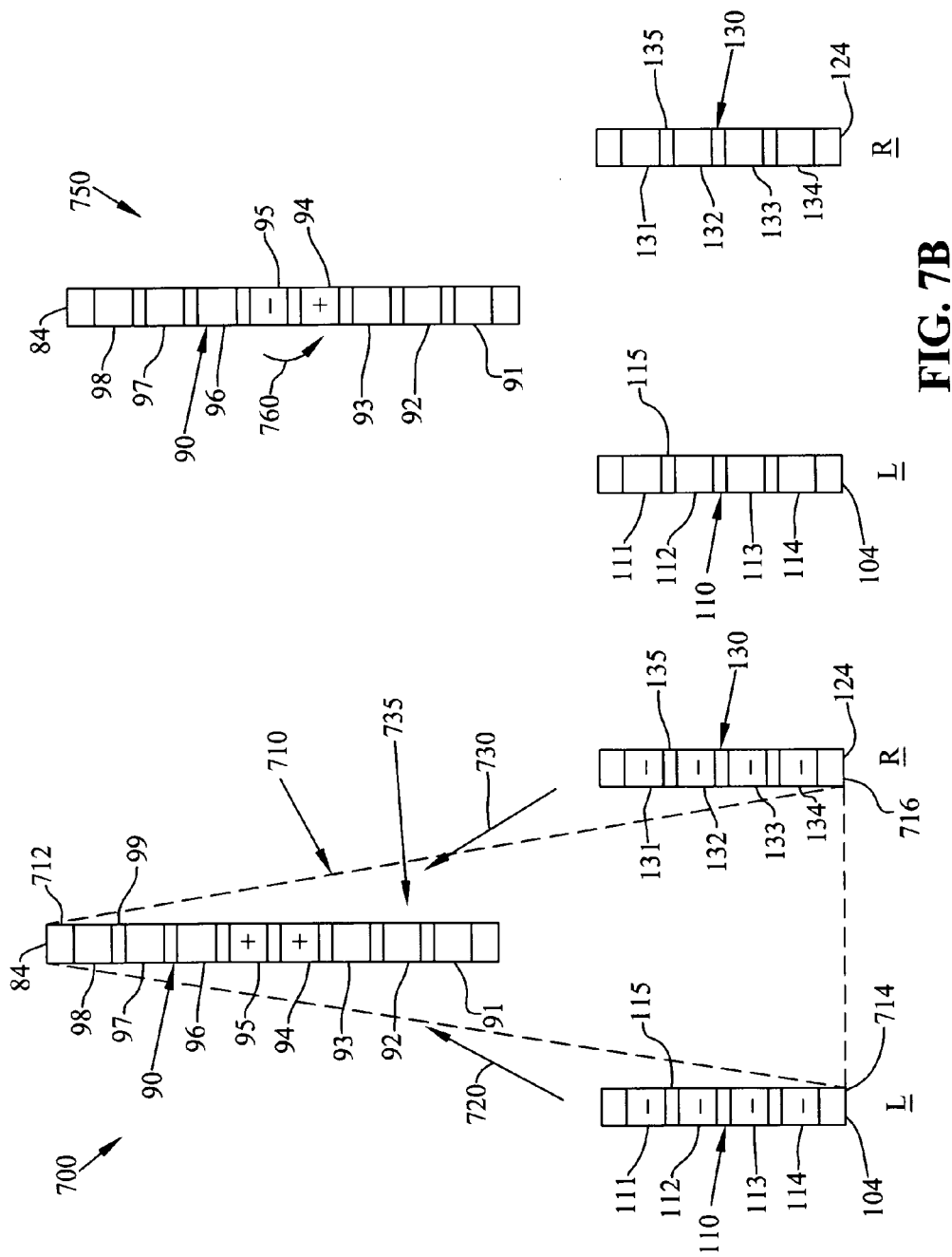
FIG. 7A is a diagram of electrode polarities representing triangular stimulation for treating low back pain.
FIG. 7B is a diagram of electrode polarities representing spinal cord stimulation for treating leg pain.

Turning now to FIG. 7A, a diagram of electrode polarities representing a triangular stimulation program or triangular stimulation (TS) 700 for treating low back pain is shown. In FIG. 7A, only the electrode portions of electrical leads 80, 100 and 120 (FIG. 1) are shown. The electrode combination shown in FIG. 7A can make up one electrode combination of a stimulation program.

TS 700 can include a group of electrodes 90 that are implanted proximate a spinal cord and a group of electrodes 110 and 130 that are implanted in subcutaneous tissue in a lumbar region 24 (FIG. 1) of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

Electrodes 90, 110 and 130 are implanted to form a polygon shape such as a triangular shape or triangle 710. Electrode 90 is located at one apex 712, electrode 110 is located at one apex 714 and electrode 130 is located at one apex 716 of triangular shape 710. Triangular shape 710 can take several different types of triangular shapes. In an embodiment, the placement of electrodes 90, 110 and 130 may form the shape of an equilateral triangle between them with a relatively constant distance between each of the electrodes. In another embodiment, the placement of electrodes 90, 110 and 130 may form the shape of an isosceles triangle between them with a relatively longer distance from electrode 90 to electrodes 110 and 130. Other polygon or triangular shapes may also be formed by electrodes 90, 110 and 130 such as scalene or obtuse.

While three groups of electrodes are shown for TS 700, more electrodes groups may be used. For example, in one embodiment, more subcutaneous electrode groups may be placed proximate the lumbar region. In another embodiment, more electrode groups may be placed proximate the spinal cord. In FIG. 7A, electrodes 90, 110 and 130 are shown relatively parallel to each other and aligned with a longitudinal axis defined by the spinal cord of the patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 94 and 95 are both defined as anodes. Electrodes 91-93 and 96-98 are neutral. Other electrodes could be defined as anodes in electrode 90. In an embodiment, more electrodes 90 could be designated as anodes. For example, all of electrodes 91-98 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively.

The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as cathodes. Fewer electrodes could be defined as cathodes in electrodes 110 and 130.

Triangular stimulation 700 causes an electrical signal with current and voltage to flow from the subcutaneous electrodes 110 and 130 proximate the lumbar region to electrodes 90 proximate the spinal cord. An electrical signal 720 with current and voltage is induced to flow from electrodes 110 to electrodes 90. An electrical signal 730 with current and voltage is induced to flow from electrodes 130 to electrodes 90. Electrical signals 720 and 730 can create a zone or field of electrical energy 735 about painful region 24 (FIG. 1). In triangular stimulation 700, the subcutaneous electrodes 110 and 130 proximate the lumbar region communicate with electrodes 90 proximate the spinal cord. The electrical communication between electrodes 90, 110 and 130 can provide effective treatment for low back pain.

The communication between the electrodes may be through nerve fibers and nerve cells in an orthodromic or antidromic manner. An orthodromic impulse runs along an axon in its normal direction, away from the soma. An antidromic impulse runs along an axon in an opposite direction, toward the soma. An antidromic impulse in an axon refers to conduction opposite to the normal, orthodromic direction.

In one embodiment, electrical signals 720 and 730 may deliver triangular stimulation and may have a frequency of 20 Hertz, a pulse width of 240 micro-seconds and an amplitude of 2.2 volts. Electrical signals 720 and 730 may have a frequency range of 5 to 100 Hertz, a pulse width range of 10 to 1000 micro-seconds and an amplitude range of 0.1 to 10.5 volts. Other frequencies, pulse widths and amplitudes can be used.

TS 700 stimulates nerves or neural tissue in the lumbar region and blocks pain signals that originate in the low back lumbar region. TS 700 provides improved pain relief for low back pain about a painful lumbar region of the patient.

TS 700 can induce "parathesia", which is a sensation of numbness or tingling in the painful regions to block the transmission of pain sensations to the brain. TS 700 can provide pain relief for axial back pain and low back pain. TS 700 can provide superior pain relief than either PSFS or SCS separately.

Triangular stimulation can create a flow of electricity or zone of electric field between the thoracic electrical lead 80 (FIG. 5) and the two lumbar electrical leads 100, 120 (FIG. 5). Triangular stimulation implies that the triangle has a zone or field of energy using current, voltage and impedance. The tip or apex 712 of the triangle 710 is in the thoracic region at the end 84 of epidural electrical lead 80. The base of the triangle 710 has two corner or base angles or apices 714 and 716 at the ends 104 and 124, respectively of electrical leads 100 and 120. Each of the base angles 714, 716 are at located proximate the center or hub where the majority of the pain is experienced by the patient on each side of the lumbar spine about lumbar-sacral region 24 (FIG. 1).

In an embodiment, group of electrodes 110 and 130 can be parallel to the lubar vertebral bodies 505 (FIG. 5) or spinal cord 14 (FIG. 5), but not necessarily equidistant to the midline or axis 550 (FIG. 5) of the lumbar spine. The use of different distances of electrodes 110 and 130 from spinal axis 550 is useful when a patient's pain is uneven in the lower back.

Triangular shape 710 can have several different shapes. In one embodiment, triangle 710 can have the shape of an isosceles triangle with two angles that are of equal measure. Other polygon shapes may also be used. Electrodes 90, 110 and 130 can be placed to form an isosceles triangle when the pain experienced by a patient is approximately equal laterally from left to right across the lower back or lumbar region 24 (FIG. 1). Patients using electrical leads that form an isosceles shape usually do not have scoliosis. A field of stimulation, zone or flow of energy 735 is occurring within this triangle.

In another embodiment, triangle 710 can have the shape of a scalene triangle with all of the angles being of unequal measure. Electrodes 90, 110 and 130 can be placed to form a scalene triangle when the pain experienced by a patient is unequal laterally from left to right across the lower back or lumbar-sacral region 24 (FIG. 1). Patients using electrical leads that form a scalene triangle may have slight scoliosis. A field of stimulation, zone or flow of energy 735 is occurring within this triangle.

In one other embodiment, triangle 710 can have the shape of an obtuse triangle with one angle being more than 90 degrees in measure. Electrodes 90, 110 and 130 can be placed to form an obtuse triangle when the pain experienced by a patient is unequal laterally from left to right across the lower back or lumbar-sacral region 24 (FIG. 1). Patients using electrical leads that form an obtuse triangle usually have moderate to severe scoliosis. A field of stimulation, zone or flow of energy 735 is occurring within this triangle.

With reference to FIG. 7B, a diagram of electrode polarities representing a spinal cord stimulation program or spinal cord stimulation (SCS) 750 for treating leg and radicular pain is shown. In FIG. 7B, only the electrode portions of electrical leads 80, 100 and 120 (FIG. 1) are shown. The electrode combination shown in FIG. 7B can make up one electrode combination of a stimulation program.

SCS 750 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrode 94 is defined as an anode and electrode 95 is defined as a cathode. Electrodes 91-93 and 96-98 are neutral. Other electrodes could be defined as anodes and cathodes in electrode 90. A larger or smaller number of electrodes could be defined as anodes and cathodes in electrode 90. For example, electrodes 91, 93, 95 and 97 may be programmed as cathodes and electrodes 92, 94, 96 and 98 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as neutral. Electrodes 131, 132, 133 and 134 are defined as neutral. No current or voltage is applied to electrodes 110 or 120.

Spinal cord stimulation 750 causes spinal cord stimulation to be applied to the patient. SCS 750 causes a current and voltage to flow from electrode 95 to electrode 94 within the epidural space proximate the spinal cord. An electrical signal 760 with current and voltage is induced to flow from electrode 95 to electrodes 94. Electrical signal 760 stimulates nerves and nerve roots along the spinal cord. SCS 750 can induce "parathesia", which is a sensation of numbness or tingling in the painful regions to block the transmission of pain sensations to the brain. SCS 750 can provide pain relief for leg and radicular pain.

In one embodiment, electrical signal 760 may deliver spinal cord stimulation and may have a frequency of 20 Hertz, a pulse width of 450 micro-seconds and an amplitude of 4.7 volts. Electrical signal 760 may have a frequency range of 5 to 100 Hertz, a pulse width range of 10 to 1000 micro-seconds and an amplitude range of 0.1 to 10.5 volts. Other frequencies, pulse widths and amplitudes can be used.

In one embodiment, triangular stimulation program or triangular stimulation 700 may run concurrently with spinal cord stimulation program or spinal cord stimulation 750. In another embodiment, triangular stimulation program or triangular stimulation 700 may be interleaved or alternated with spinal cord stimulation program or spinal cord stimulation 750. In one other embodiment, triangular stimulation program or triangular stimulation 700 may be run separately from spinal cord stimulation program or spinal cord stimulation 750. In another embodiment, triangular stimulation 700 may be run with concurrently or separately with SCS and/or another PSFS program.

With reference to both FIGS. 7A and 7B, each area around apices 712, 714 and 716 can be regarded as a hub of energy. When triangular stimulation 700 runs concurrently with spinal cord stimulation 750, the electrical signals 720, 730 and 760 can interact creating an overlapping energy field. The overlapping of electrical signals 720, 730 and 760 can create amplitude spikes within triangular area 710. If the spikes occur close to the spine, they may cause more intercostal and/or ventral stimulation. Ventral stimulation or ventral parathesia is an uncomfortable parathesia that is felt by the patient in the thorax and abdomen. Ventral stimulation occurs when the dorsal root entry zone is within the flow of electricity.

The use of cathodes in the electrodes 90 and anodes in electrodes 110 and 130 has experimentally been shown in general to cause more leg pain and uncomfortable intercostal stimulation than the use of anodes in electrodes 90 and cathodes in electrodes 110 and 130. In some cases, such as with patients that have spinal stenosis or a spinal cord injury, the use of cathodes in electrodes 90 and anodes in electrodes 110 and 130 provides improved pain relief due to deeper penetration of the electrical signals into the innervated areas.

Figure 7C:
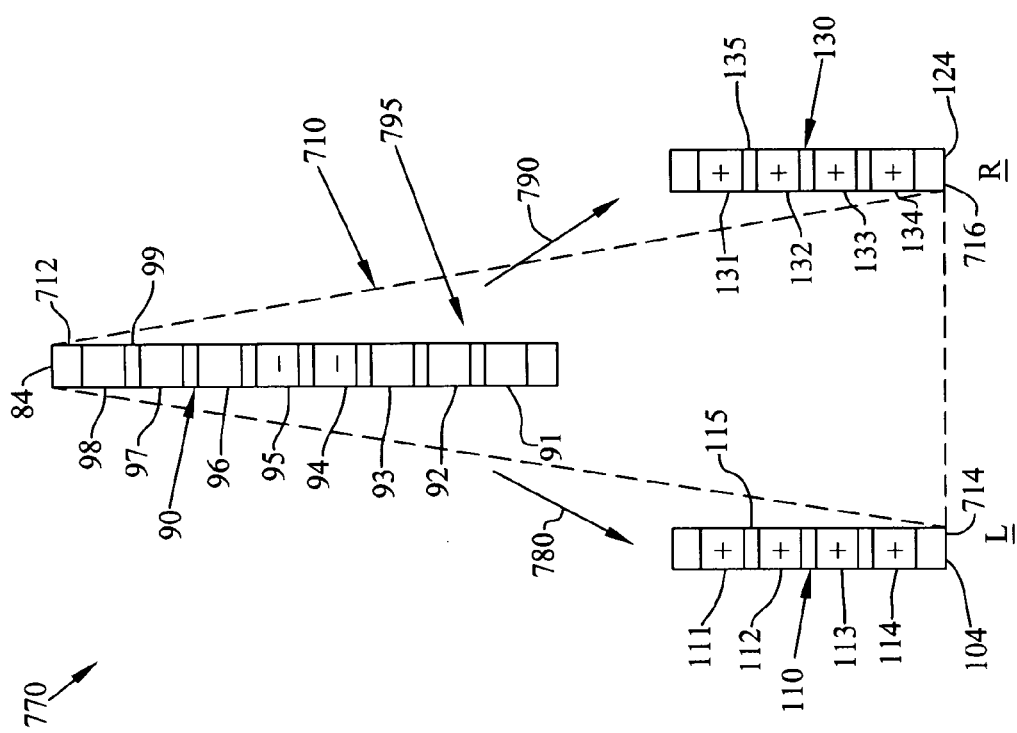
FIG. 7C is another diagram of electrode polarities representing triangular stimulation for treating low back pain.

With reference to FIG. 7C, another diagram of electrode polarities representing a triangular stimulation program or triangular stimulation (TS) 770 for treating low back pain is shown. In FIG. 7C, only the electrode portions of electrical leads 80, 100 and 120 (FIG. 1) are shown. The electrode combination shown in FIG. 7C can make up one electrode combination of a stimulation program.

Triangular stimulation 770 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

Electrodes 90, 110 and 130 are implanted arranged to form a generally triangular shape 710. Electrode 90 is located at one apex 712, electrode 110 is located at one apex 714 and electrode 130 is located at one apex 716 of triangular shape 710. Triangular shape 710 can take several different types of triangular shapes. In an embodiment, the placement of electrodes 90, 110 and 130 may form the shape of an equilateral triangle between them with a relatively constant distance between each of the electrodes. In another embodiment, the placement of electrodes 90, 110 and 130 may form the shape of an isosceles triangle between them with a relatively longer distance from electrode 90 to electrodes 110 and 130. Other triangular shapes may also be formed by electrodes 90, 110 and 130 such as scalene or obtuse. Other polygon shapes may also be formed.

While three groups of electrodes are shown for TS 770, more electrodes groups may be used. For example, in one embodiment, more subcutaneous electrode groups may be placed proximate the lumbar region. In another embodiment, more electrode groups may be placed proximate the spinal cord. In FIG. 7C, electrodes 90, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 94 and 95 are both defined as cathodes. Electrodes 91-93 and 96-98 are neutral. Other electrodes could be defined as cathodes in electrode 90. In an embodiment, more electrodes 90 could be designated as cathodes. For example, all of electrodes 91-98 may be programmed as cathodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as anodes. Electrodes 131, 132, 133 and 134 are defined as anodes. Fewer electrodes could be defined as anodes in electrodes 110 and 130.

Triangular stimulation 770 causes an electrical signal with current and voltage to flow from electrode 90 proximate the spinal cord to the subcutaneous electrodes 110 and 130 proximate the lumbar region. An electrical signal 780 with current and voltage is induced to flow from electrodes 90 to electrodes 110. An electrical signal 790 with current and voltage is induced to flow from electrodes 90 to electrodes 130. Electrical signals 780 and 790 can create a zone or field of electrical energy 795 about painful region 24 (FIG. 1).

In one embodiment, electrical signals 780 and 790 may deliver triangular stimulation and may have a frequency of 20 Hertz, a pulse width of 240 micro-seconds and an amplitude of 2.2 volts. Electrical signals 780 and 790 may have a frequency range of 5 to 100 Hertz, a pulse width range of 10 to 1000 micro-seconds and an amplitude range of 0.1 to 10.5 volts. Other frequencies, pulse widths and amplitudes can be used.

Triangular stimulation 770 stimulates nerves or neural tissue in the lumbar region and blocks pain signals that originate in the low back lumbar region. TS 770 provides improved pain relief for low back pain about a painful lumbar region of the patient.

With reference to FIG. 7D, another diagram of electrode polarities representing a triangular stimulation program, triangular stimulation or quadrilateral stimulation (QS) 300 for treating low back pain is shown. In FIG. 7D, only the electrode portions of the electrical leads are shown. The electrode combination shown in FIG. 7D can make up one electrode combination of a stimulation program.

Quadrilateral stimulation 300 can include a group of electrodes 310 and 320 that are implanted proximate a spinal cord and a group of electrodes 110 and 130 that are implanted in subcutaneous tissue in a lumbar region of the lower back. Electrodes 310 and 320 can be implanted in epidural space 540 (FIG. 5) proximate spinal cord 14. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

Electrodes 310, 320, 110 and 130 are implanted arranged to form a generally triangular shape or more specifically a trapezoidal quadrilateral shape 330. Electrode 310 is located at one apex 334, electrode 320 is located at apex 332, electrode 110 is located at one apex 336 and electrode 130 is located at one apex 338 of quadrilateral shape 330. Shape 330 can take several different types of polygon shapes. For example, the placement of electrodes 310, 320 110 and 130 may form a trapezoid, rhombus, square, rectangle, parallelogram or any other generally four sided shape or a five, six, seven, eight, nine or ten sided shape.

While four groups of electrodes are shown for QS 300, more electrodes groups may be used. For example, in one embodiment, more subcutaneous electrode groups may be placed proximate the lumbar region. In another embodiment, more electrode groups may be placed proximate the spinal cord. In FIG. 7D, electrodes 310, 320, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 310 have a generally elongated cylindrical shape and include four circumferential electrodes that are separated by a region of insulation 309. Electrodes 310 include individual electrodes 305, 306, 307 and 308. Each of electrodes 305-308 is electrically connected to implantable device 40 (FIG. 1) through an electrical lead. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 306 and 307 are both defined as anodes. Electrodes 305 and 308 are neutral. Other electrodes could be defined as anodes in electrodes 310. In an embodiment, more electrodes 310 could be designated as anodes. For example, all of electrodes 305-308 may be programmed as anodes in one embodiment.

Electrodes 320 have a generally elongated cylindrical shape and include four circumferential electrodes that are separated by a region of insulation 325. Electrodes 320 include individual electrodes 321, 322, 323 and 324. Each of electrodes 321-324 is electrically connected to implantable device 40 (FIG. 1) through an electrical lead. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 322 and 323 are both defined as anodes. Electrodes 321 and 324 are neutral. Other electrodes could be defined as anodes in electrodes 320. In an embodiment, more electrodes 320 could be designated as anodes. For example, all of electrodes 321-324 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as cathodes. Fewer electrodes could be defined as cathodes in electrodes 110 and 130.

QS 300 causes an electrical signal with current and voltage to flow from electrodes 110 and 130 proximate the lumbar region to electrodes 310 and 330 proximate the spinal cord. An electrical signal 340 with current and voltage is induced to flow from electrodes 110 to electrodes 310 and 320. An electrical signal 350 with current and voltage is induced to flow from electrodes 130 to electrodes 310 and 320. Electrical signals 340 and 350 can create a zone or field of electrical energy 360 about painful region 24 (FIG. 1).

In one embodiment, electrical signals 340 and 350 may deliver quadrilateral stimulation and may have a frequency of 20 Hertz, a pulse width of 240 micro-seconds and an amplitude of 2.2 volts. Electrical signals 340 and 350 may have a frequency range of 5 to 100 Hertz, a pulse width range of 10 to 1000 micro-seconds and an amplitude range of 0.1 to 10.5 volts. Other frequencies, pulse widths and amplitudes can be used.

QS 300 stimulates nerves or neural tissue in the lumbar region and blocks pain signals that originate in the low back lumbar region. QS 300 provides improved pain relief for low back pain about a painful lumbar region of the patient.

FIG. 8A, illustrates a diagram of electrode polarities representing a flow stimulation program or flow stimulation (FS) 800 for treating low back pain. Flow stimulation 800 uses all anodes on one electrical lead and all cathodes on another electrical lead. In FIG. 8A, only the electrode portions of electrical leads 80, 100 and 120 (FIG. 1) are shown. The electrode combination shown in FIG. 8A can make up one electrode combination of a stimulation program.

Flow stimulation 800 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for FS 800, more or less electrodes groups may be used. For example, in one embodiment, more subcutaneous electrode groups may be placed proximate the lumbar region. In FIG. 8A, electrodes 90, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as anodes. Fewer electrodes could be defined as cathodes in electrodes 110. Fewer electrodes could be designated as anodes in electrodes 130.

FS 800 causes an electrical signal with current and voltage to flow between the subcutaneous electrodes 110 and 130 proximate the lumbar region. An electrical signal 810 with current and voltage is induced to flow from electrodes 110 to electrodes 130. FS 800 stimulates nerves or neural tissue in the lumbar region and blocks pain signals that originate in the low back lumbar region. FS 800 can induce "parathesia", which is a sensation of numbness or tingling in the painful regions to block the transmission of pain sensations to the brain. FS 800 can provide pain relief for axial back pain and low back pain.

In one embodiment, electrical signal 810 may deliver flow stimulation and may have a frequency of 20 Hertz, a pulse width of 240 micro-seconds and an amplitude of 1.8 volts. Electrical signal 810 may have a frequency range of 5 to 100 Hertz, a pulse width range of 10 to 1000 micro-seconds and an amplitude range of 0.1 to 10.5 volts. Other frequencies, pulse widths and amplitudes can be used.

With reference to FIG. 8B, another diagram of electrode polarities representing a flow stimulation program or flow stimulation (FS) 820 for treating low back pain is shown. In FIG. 8B, only the electrode portions of electrical leads 80, 100 and 120 (FIG. 1) are shown. The electrode combination shown in FIG. 8B can make up one electrode combination of a stimulation program.

Flow stimulation 820 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for FS 820, more or less electrodes groups may be used. For example, in one embodiment, more subcutaneous electrode groups may be placed proximate the lumbar region. In FIG. 8B, electrodes 90, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as anodes. Electrodes 131, 132, 133 and 134 are defined as cathodes. Fewer electrodes could be defined as anodes in electrodes 110. Fewer electrodes could be designated as cathodes in electrodes 130.

FS 820 causes an electrical signal with current and voltage to flow between the subcutaneous electrodes 110 and 130 proximate the lumbar region. An electrical signal 830 with current and voltage is induced to flow from electrodes 130 to electrodes 110. FS 820 stimulates nerves or neural tissue in the lumbar region and blocks pain signals that originate in the low back lumbar region.

FS 820 stimulates nerves or neural tissue in the lumbar region and blocks pain signals that originate in the low back lumbar region. FS 820 can induce "parathesia", which is a sensation of numbness or tingling in the painful regions to block the transmission of pain sensations to the brain. FS 820 can provide pain relief for axial back pain and low back pain.

In one embodiment, electrical signal 830 may deliver flow stimulation and may have a frequency of 20 Hertz, a pulse width of 240 micro-seconds and an amplitude of 3.5 volts. Electrical signal 830 may have a frequency range of 5 to 100 Hertz, a pulse width range of 10 to 1000 micro-seconds and an amplitude range of 0.1 to 10.5 volts. Other frequencies, pulse widths and amplitudes can be used.

In one embodiment, flow stimulation program or flow stimulation 800 may run concurrently with spinal cord stimulation program or spinal cord stimulation 750. In another embodiment, flow stimulation program or flow stimulation 820 may run concurrently with spinal cord stimulation program or spinal cord stimulation 750. In an embodiment, flow stimulation program or flow stimulation 800 may be interleaved or alternated with flow stimulation program or flow stimulation 820 and spinal cord stimulation program or spinal cord stimulation 750. In one other embodiment, flow stimulation program or flow stimulation 800 may be run separately from flow stimulation program or flow stimulation 820 and spinal cord stimulation program or spinal cord stimulation 750. In another other embodiment, flow stimulation program or flow stimulation 800 and stimulation program or flow stimulation 820 may be alternatively used with spinal cord stimulation program or spinal cord stimulation 750, TS700, TS770 or another PSFS program.

FIG. 9A, illustrates a diagram of electrode polarities representing an example of one type of peripheral subcutaneous field stimulation program (PSFS) 900. PSFS 900 uses a mixture of anodes and cathodes on each electrical lead. In FIG. 9A, only the electrode portions of electrical leads 80, 100 and 120 (FIG. 1) are shown. The electrode combination shown in FIG. 9A can make up one electrode combination of a stimulation program.

PSFS 900 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for PSFS 900, more or less electrodes groups may be used. For example, in one embodiment, more subcutaneous electrode groups may be placed proximate the lumbar region. In FIG. 9A, electrodes 90, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 112 and 132 are defined as cathodes. Electrodes 113 and 133 are defined as anodes. Electrodes 111, 114, 131 and 134 are neutral and have no polarity. A larger or smaller number of electrodes could be defined as anodes and cathodes in electrodes 110 and 130.

PSFS 900 causes an electrical signal with current and voltage to flow about or around each electrode 110 and 130 proximate the lumbar region. An electrical signal 910 with current and voltage is induced to flow from electrode 112 to electrode 113. An electrical signal 920 with current and voltage is induced to flow from electrode 132 to electrode 133.

In one embodiment, electrical signals 910 and 920 may deliver PSFS and may have a frequency of 20 Hertz, a pulse width of 240 micro-seconds and an amplitude of 2.2 volts. Other frequencies, pulse widths and amplitudes can be used.

In an embodiment, electrical signals 910 and 920 may be different. Implantable device 40 (FIG. 1) may be programmed to deliver a different electrical signals with different electrical parameters to each group of electrodes 110 and 130. This may be called a split program with one program delivering electrical signals to electrodes 110 and another program delivering electrical signals to electrodes 130. For example, in one embodiment, electrical signal 910 may have a frequency of 20 Hertz, a pulse width of 240 micro-seconds and an amplitude of 2.2 volts and electrical signal 920 may have a frequency of 40 Hertz, a pulse width of 420 micro-seconds and an amplitude of 4.4 volt. The use of different electrical signals for each group of electrodes is useful when the pain experienced by a patient is uneven. If a patient experiences more pain in the right lower back region, electrical signal 920 may be adjusted to provide a larger electric field or zone of electrical energy.

PSFS 900 can stimulate nerves or neural tissue in the lumbar region and block pain signals that originate in the low back lumbar region. PSFS 900 can induce "parathesia", which is a sensation of numbness or tingling in the painful regions to block the transmission of pain sensations to the brain. PSFS can provide pain relief for back pain.

In one embodiment, PSFS 900 may run concurrently with spinal cord stimulation program or spinal cord stimulation 750. In another embodiment, PSFS 900 may be may be interleaved or alternated with flow stimulation program or flow stimulation 800, flow stimulation program or flow stimulation 820, spinal cord stimulation program or spinal cord stimulation 750 and triangular stimulation 700 or 770. In one other embodiment, PSFS 900 may be run separately from flow stimulation program or flow stimulation 800, flow stimulation program or flow stimulation 820, spinal cord stimulation program or spinal cord stimulation 750 and triangular stimulation program or triangular stimulation 700 or 770. In another embodiment, PSFS 900 may be combined with triangular stimulation program or triangular stimulation 700 or 770.

FIG. 9B, illustrates another diagram of electrode polarities representing an example of one type of peripheral subcutaneous field stimulation program (PSFS) 925. PSFS 925 uses a mixture of anodes and cathodes on each lead. In FIG. 9B, only the electrode portions of electrical leads 80, 100 and 120 (FIG. 1) are shown. The electrode combination shown in FIG. 9B can make up one electrode combination of a stimulation program.

PSFS 925 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for PSFS 925, more or less electrodes groups may be used. For example, in one embodiment, more subcutaneous electrode groups may be placed proximate the lumbar region. In FIG. 9B, electrodes 90, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 90 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120, respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 112, 114, 131 and 133 are defined as cathodes. Electrodes 111, 113, 132 and 134 are defined as anodes.

PSFS 925 causes an electrical signal with current and voltage to flow about or around each electrode 110 and 130 proximate the lumbar region. An electrical signal 930 with current and voltage is induced to flow from electrode 112 to electrodes 111 and 113 and from electrode 114 to electrodes 111 and 113. An electrical signal 940 with current and voltage is induced to flow from electrode 131 to electrodes 132 and 134 and from electrode 133 to electrodes 132 and 134.

In one embodiment, electrical signals 930 and 940 may deliver PSFS and may have a frequency of 20 Hertz, a pulse width of 240 micro-seconds and an amplitude of 2.2 volts. Other frequencies, pulse widths and amplitudes can be used.

PSFS 925 can stimulate nerves or neural tissue in the lumbar region and block pain signals that originate in the low back lumbar region. PSFS 925 can induce "parathesia", which is a sensation of numbness or tingling in the painful regions to block the transmission of pain sensations to the brain. PSFS can provide pain relief for back pain.

In one embodiment, PSFS 925 may run concurrently with spinal cord stimulation program or spinal cord stimulation 750. In another embodiment, PSFS 925 may be may be interleaved or alternated with flow stimulation program or flow stimulation 800, flow stimulation program or flow stimulation 820, spinal cord stimulation program or spinal cord stimulation 750 and triangular stimulation 700 or 770. In one other embodiment, PSFS 925 may be run separately from flow stimulation program or flow stimulation 800, flow stimulation program or flow stimulation 820, spinal cord stimulation program or spinal cord stimulation 750 and triangular stimulation program or triangular stimulation 700 or 770. In another embodiment, PSFS 920 may be combined with triangular stimulation program or triangular stimulation 700 or 770.

FIG. 9C, illustrates another diagram of electrode polarities representing an example of one type of peripheral subcutaneous field stimulation program (PSFS) 950. PSFS 950 uses a mixture of anodes and cathodes on each lead. In FIG. 9C, only the electrode portions of electrical leads 80, 100 and 120

(FIG. 1) are shown. The electrode combination shown in FIG. 9C can make up one electrode combination of a stimulation program.

PSFS 950 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for PSFS 950, more or less electrodes groups may be used. For example, in one embodiment, more subcutaneous electrode groups may be placed proximate the lumbar region. In FIG. 9C, electrodes 90, 110 and 130 are shown relatively parallel to each other and aligned with a longitudinal axis defined the spinal cord of a patient (FIG. 1). It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 112, 113, 114, 132, 133 and 134 are defined as cathodes. Electrodes 111 and 131 are defined as anodes.

PSFS 950 causes an electrical signal with current and voltage to flow about or around each electrode 110 and 130 proximate the lumbar region. An electrical signal 960 with current and voltage is induced to flow from electrodes 112, 113 and 114 to electrode 111. An electrical signal 970 with current and voltage is induced to flow from electrodes 132, 133 and 134 to electrode 131.

In one embodiment, electrical signals 960 and 970 may deliver PSFS and may have a frequency of 20 Hertz, a pulse width of 240 micro-seconds and an amplitude of 2.2 volts. Other frequencies, pulse widths and amplitudes can be used.

PSFS 950 can stimulate nerves or neural tissue in the lumbar region and block pain signals that originate in the low back lumbar region. PSFS 950 can induce "parathesia", which is a sensation of numbness or tingling in the painful regions to block the transmission of pain sensations to the brain. PSFS 950 can provide pain relief for back pain.

In one embodiment, PSFS 950 may run concurrently with spinal cord stimulation program or spinal cord stimulation 750. In another embodiment, PSFS 950 may be may be interleaved or alternated with flow stimulation program or flow stimulation 800, flow stimulation program or flow stimulation 820, spinal cord stimulation program or spinal cord stimulation 750 and triangular stimulation 700 or 770. In one other embodiment, PSFS 950 may be run separately from flow stimulation program or flow stimulation 800, flow stimulation program or flow stimulation 820, spinal cord stimulation program or spinal cord stimulation 750 and triangular stimulation program or triangular stimulation 700 or 770. In another embodiment, PSFS 950 may be combined with triangular stimulation program or triangular stimulation 700 or 770.

FIG. 10A, illustrates an additional diagram of electrode polarities representing an example of one type of field flow stimulation program or field flow stimulation (FFS) 1000. FFS 1000 uses a mixture of anodes and cathodes on one electrical lead and all anodes or cathodes on the other electrical lead. Each electrical lead will have its own stimulation program. In FIG. 10A, only the electrode portions of electrical leads 80, 100 and 120 (FIG. 1) are shown. The electrode combination shown in FIG. 10A can make up one electrode combination of a stimulation program.

FFS 1000 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for FFS 1000, more or less electrodes groups may be used. For example, in one embodiment, more subcutaneous electrode groups may be placed proximate the lumbar region. In FIG. 10A, electrodes 90, 110 and 130 are shown relatively parallel to each other and aligned with a longitudinal axis defined the spinal cord of a patient (FIG. 1). It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Group of electrodes 110 include individual electrodes 111, 112, 113 and 114. Group of electrodes 130 include individual electrodes 131, 132, 133 and 134. Each of electrodes 111-114 and 131-134 are electrically connected to implantable device 40 (FIG. 1) through electrical leads 100 and 120, respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 112, 114, 131, 132, 133 and 134 are defined as cathodes. Electrodes 111 and 113 are defined as anodes. In an embodiment, fewer of electrodes 130 could be designated as cathodes. For example, only electrodes 131, 132 and 133 may be programmed as cathodes.

FFS 1000 causes an electrical signal with current and voltage to flow about or around each electrode 110 and between electrodes 130 and 110 proximate the lumbar region. An electrical signal 1010 with current and voltage is induced to flow from electrodes 131, 132, 133 and 134 to electrodes 111 and 113. An electrical signal 1020 with current and voltage is induced to flow from electrodes 112 and 114 to electrodes 111 and 113. Electrical signals 1010 and 1020 are generated by separate stimulation programs running on the implantable device.

In one embodiment, electrical signals 1010 and 1020 may deliver FFS and may have a frequency of 20 Hertz, a pulse width of 240 micro-seconds and an amplitude of 2.2 volts. Other frequencies, pulse widths and amplitudes can be used.

FFS 1000 can stimulate nerves or neural tissue in the lumbar and sacral region and block pain signals that originate in the low back lumbar region. FFS 1000 can induce "parathesia", which is a sensation of numbness or tingling in the painful regions to block the transmission of pain sensations to the brain. FFS can provide pain relief for back pain.

In one embodiment, FFS 1000 may run concurrently with spinal cord stimulation program or spinal cord stimulation 750. In another embodiment, FFS 1000 may be may be interleaved or alternated with flow stimulation program or flow stimulation 800, flow stimulation program or flow stimulation 820, spinal cord stimulation program or spinal cord stimulation 750 and triangular stimulation 700 or 770. In one other embodiment, FFS 1000 may be run separately from flow stimulation program or flow stimulation 800, flow stimulation program or flow stimulation 820, spinal cord stimulation program or spinal cord stimulation 750 and triangular stimulation program or triangular stimulation 700 or 770. In another embodiment, FFS 1000 may be combined with triangular stimulation program or triangular stimulation 700 or 770.

FIG. 10B, illustrates an additional diagram of electrode polarities representing an example of one type of peripheral subcutaneous field flow stimulation program or peripheral subcutaneous field flow stimulation (FFS) 1050. FFS 1050 uses a mixture of anodes and cathodes on one electrical lead and all anodes or cathodes on the other electrical lead. In FIG. 10B, only the electrode portions of electrical leads 80, 100 and 120 (FIG. 1) are shown. The electrode combination shown in FIG. 10B can make up one electrode combination of a stimulation program.

FFS 1050 can include a group of electrodes 90 that are implanted proximate a spinal cord and a group of electrodes 110 and 130 that are implanted in subcutaneous tissue in a lumbar region of the lower back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

While three groups of electrodes are shown for FFS 1050, more or less electrodes groups may be used. For example, in one embodiment, more subcutaneous electrode groups may be placed proximate the lumbar region. In FIG. 10B, electrodes 90, 110 and 130 are shown relatively parallel to each other and aligned with a longitudinal axis defined by the spinal cord of a patient. It is understood that at least electrodes 110 and 130 may be oriented at other angles that are inwardly or outwardly disposed to the axis defined by the spinal cord of the patient.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 1) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 91, 92, 93, 94, 95, 96, 97 and 98 are defined as neutral. No current or voltage is applied to electrodes 90.

Electrodes 110 and 130 also have a generally elongated cylindrical shape and include four circumferential electrodes that are separated by regions of insulation 115 and 135 respectively. Group of electrodes 110 include individual electrodes 111, 112, 113 and 114. Group of electrodes 130 include individual electrodes 131, 132, 133 and 134. Each of electrodes 111-114 and 131-134 are electrically connected to implantable device 40 (FIG. 1) through electrical leads 100 and 120 respectively. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 131 and 133 are defined as cathodes. Electrodes 111, 112, 133, 114, 132 and 134 are defined as anodes. In an embodiment, fewer of electrodes 110 could be designated as anodes. For example, only electrodes 111, 112 and 113 may be programmed as anodes.

FFS 1050 causes an electrical signal with current and voltage to flow about or around each electrode 110 and between electrodes 130 and 110 proximate the lumbar region. An electrical signal 1060 with current and voltage is induced to flow from electrodes 131 and 133 to electrodes 111, 112, 133 and 114 (collectively group of electrodes 110). An electrical signal 1070 with current and voltage is induced to flow from electrodes 131 and 133 to electrodes 132 and 134. Electrical signals 1060 and 1070 are generated by separate stimulation programs running on the implantable device.

In one embodiment, electrical signals 1060 and 1070 may deliver FFS and may have a frequency of 20 Hertz, a pulse width of 240 micro-seconds and an amplitude of 2.2 volts. Other frequencies, pulse widths and amplitudes can be used.

FFS 1050 can stimulate nerves or neural tissue in the lumbar region and block pain signals that originate in the low back lumbar region. FFS 1050 can induce "parathesia", which is a sensation of numbness or tingling in the painful regions to block the transmission of pain sensations to the brain. FFS can provide pain relief for back pain.

In one embodiment, FFS 1050 may run concurrently with spinal cord stimulation program or spinal cord stimulation 750. In another embodiment, FFS 1050 may be interleaved or alternated with flow stimulation program or flow stimulation 800, flow stimulation program or flow stimulation 820, spinal cord stimulation program or spinal cord stimulation 750 and triangular stimulation 700 or 770. In one other embodiment, FFS 1050 may be run separately from flow stimulation program or flow stimulation 800, flow stimulation program or flow stimulation 820, spinal cord stimulation program or spinal cord stimulation 750 and triangular stimulation program or triangular stimulation 700 or 770. In another embodiment, FFS 1050 may be combined with triangular stimulation program or triangular stimulation 700 or 770.

FIG. 11 illustrates a flow chart of a method 1100 for providing pain relief for a patient using system 10 (FIG. 1) and programming implantable device 40 (FIG. 1) using programming device 200 (FIG. 1). Method 1100 provides a method for selecting one or more neurostimulation programs that maximize pain relief for a patient using a combination of one or more of spinal cord stimulation, triangular stimulation, flow stimulation or peripheral subcutaneous field stimulation or peripheral subcutaneous split flow stimulation.

At step 1102, electrical leads are implanted in the patient. Step 1102 can include the implantation of electrical leads in an epidural space proximate a spinal cord and in subcutaneous tissue proximate a lumbar region by a physician.

At step 1104, the triangular stimulation 700 (FIG. 7A) is programmed. Step 1104 includes inputting the triangular stimulation program to the programming device and transferring the triangular stimulation program to the implantable device.

Next, the triangular stimulation program is tested on the patient in step 1106. The triangular stimulation program is run by the implantable device such that electrical signals are sent to the electrodes within the patient.

Feedback from the patient is requested in decision step 1108. The patient is queried by a physician or clinician as to if they are experiencing any uncomfortable ventral stimulation or intercostal stimulation. Ventral stimulation or ventral parathesia is an uncomfortable parathesia that is felt by the patient in the thorax and abdomen. Ventral stimulation occurs when the dorsal root entry zone is within the flow of electricity. If the patient does not experience any ventral stimulation, method 1100 proceeds to decision step 1110. If the patient experiences ventral stimulation, method 1100 proceeds to decision step 1116.

At decision step 1110, the patient is queried as to if the stimulation is laterally even about both the left and right sides of their body without any stinging stimulation. If the stimulation is laterally even, method 1100 proceeds to decision step 1112. If the stimulation is not laterally even, method 1100 proceeds to step 1118.

The patient is asked in decision step 1112 if the triangular stimulation is covering or blocking their pain and providing pain relief. If the patient is satisfied with the level of pain relief provided by triangular stimulation, the triangular stimulation program can be set as a permanent program to be used by the patient at step 1120. If the patient not is satisfied with the level of pain relief provided by triangular stimulation, method 1100 proceeds to step 1114 where the patient and the physician may consider revising the placement of one or more of the electrical leads.

At decision step 1116, the patient is queried by a physician or clinician as to if they need coverage over a broad area of pain or if the pain they are experiencing is focused in a specific focal area. If the patient answers that they have a broad area of pain to be treated, method 1100 proceeds to step 1122 where peripheral subcutaneous field stimulation (PSFS) 900 (FIG. 9) is programmed using programming device 200 and implantable device 40. If the patient answers that they have a specific focal area of pain to be treated, method 1100 proceeds to step 1124 where flow stimulation 800 or 820 (FIG. 8A, 8B) is programmed using programming device 200 and implantable device 40.

After flow stimulation is programmed in step 1124, the flow stimulation program or flow stimulation is tested on the patient in step 1126. Next, the patient is asked in decision step 1128 if the flow stimulation is covering or blocking their pain and providing pain relief. If the patient is satisfied with the level of pain relief provided by flow stimulation, the flow stimulation program can be set as a permanent program to be used by the patient at step 1120. If the patient not is satisfied with the level of pain relief provided by flow stimulation, method 1100 proceeds to step 1114 where the patient and the physician may consider revising the placement of one or more of the electrical leads.

After PSFS is programmed in step 1122, PSFS is tested on the patient in step 1140. Next, the patient is asked in decision step 1142 as to if the stimulation is laterally even about both the left and right sides of their body without any stinging stimulation. If the stimulation is laterally even, method 1100 proceeds to decision step 1128. If the stimulation is not laterally even, method 1100 proceeds to step 1118.

In decision step 1128, the patient is queried if the PSFS stimulation is covering or blocking their pain and providing pain relief. If the patient is satisfied with the level of pain relief provided by PSFS, the PSFS program can be set as a permanent program to be used by the patient at step 1120. If the patient not is satisfied with the level of pain relief provided by PSFS, method 1100 proceeds to step 1114 where the patient and the physician may consider revising the placement of one or more electrical leads.

If the stimulation is not laterally even at decision step 1142, PSFS 900 is split into separate PSFS programs that each run individually in step 1118. In step 1118, the electrical signals delivered to electrodes 110 and 130 (FIG. 9A) are different. For example, the amplitude delivered to electrodes 110 may be less than the amplitude delivered to electrodes 130. In another example, the pulse width delivered to electrodes 110 may be less than the pulse width delivered to electrodes 130. In another example, different electrodes may be programmed as anodes and cathodes in electrodes 110 than in electrodes 130. Next, the split programs are tested on the patient in step 1144.

In decision step 1128, the patient is queried if the split PSFS is covering or blocking their pain and providing pain relief. If the patient is satisfied with the level of pain relief provided by split PSFS, the split PSFS program can be set as a permanent program to be used by the patient at step 1120. If the patient not is satisfied with the level of pain relief provided by split PSFS, method 1100 proceeds to step 1114 where the patient and the physician may consider revising the placement of one or more electrical leads.

Method 1100 provides a technique for programming a combination of epidural spinal cord electrical leads and subcutaneous electrical leads. Method 1100 minimizes the effects of undesired ventral or intercostal stimulation and of uneven lateral stimulation with regards to stinging stimulation. Method 1100 optimizes the level of pain relief by a patient using one or a combination of triangular stimulation, flow stimulation, spinal cord stimulation, peripheral subcutaneous field stimulation and peripheral subcutaneous field flow stimulation.

Figure 12:
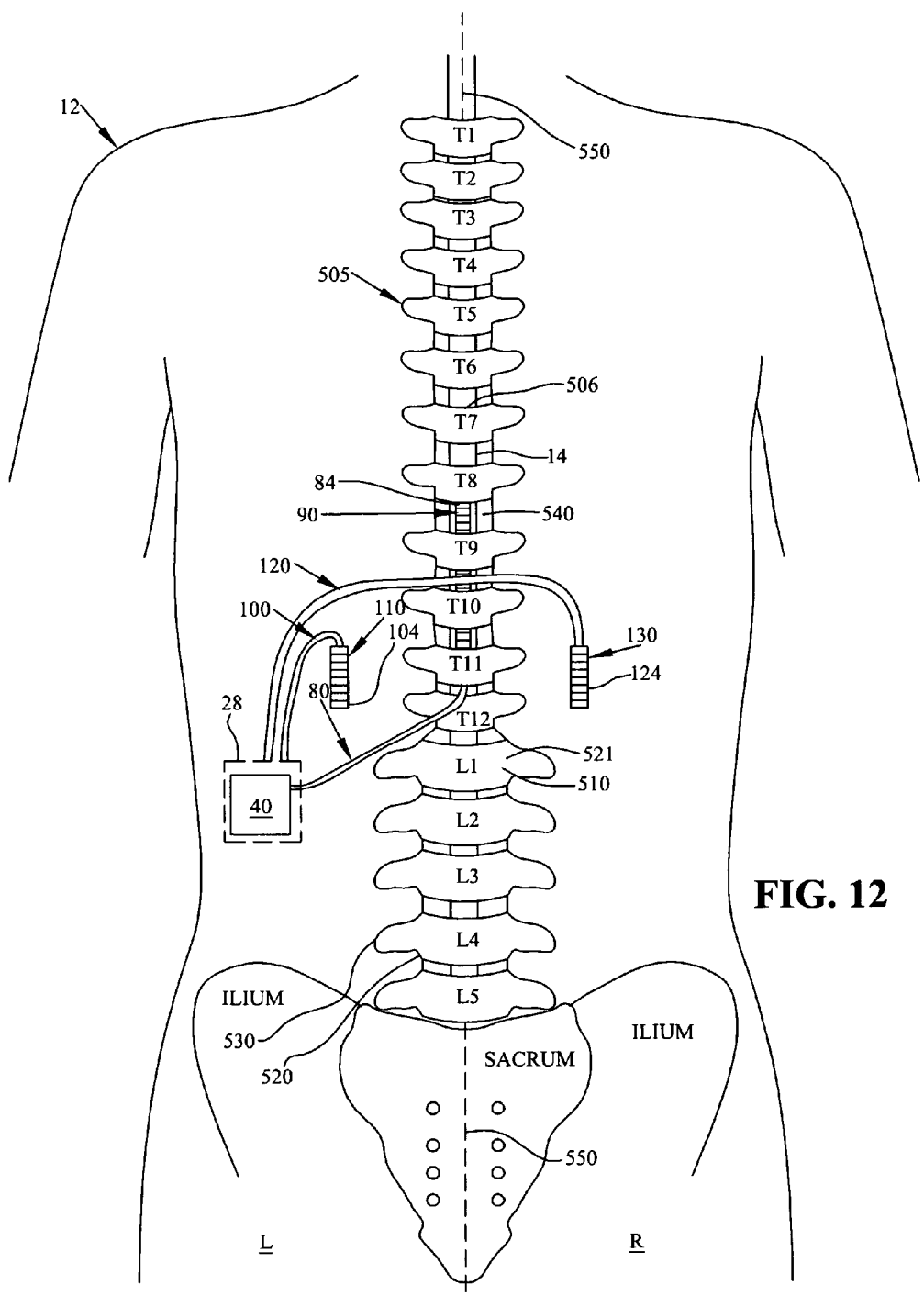
FIG. 12 is a detailed diagram of an electrical lead implanted in an epidural space in a thoracic region and pair of subcutaneous electrical leads implanted in subcutaneous tissue in a thoracic region showing the specific anatomical placement of the electrical leads in an embodiment.

FIG. 12 illustrates the anatomical placement of electrical leads for triangular stimulation in a thoracic region of a patient. In one embodiment, the electrical leads in FIG. 12 can be used to treat degenerative scoliosis or kyphosis. A posterior view of patent 12 is shown in FIG. 12. Patient 12 has a vertebrae column 505 that contains individual vertebrae 510. The vertebrae include the thoracic vertebrae T1, T2, T3, T4, T5, T6, T7, T8, T9, T10, T11 and T12 (T1-T12), the lumbar vertebrae L1, L2, L3, L4 and L5 (L1-L5) and the sacrum. The location of the ilium and iliac crest are also shown. The discs that are located between the vertebrae are omitted in FIG. 12 in order to show additional detail.

Spinal cord 14 extends lengthwise through the vertebrae column 505. Spinal cord 14 can have a midline or spinal axis 550 that is parallel with vertebrae column 505. Axis 550 can divide the body of patient 12 into a left half L and a right half R. Each vertebra has a vertebral foramen 506. The spinal cord 14 extends through each vertebral foramen 506. An epidural space 540 surrounds the spinal cord 14.

Each vertebra T1-T12 and L1-L5 has a pair of lateral pedicels 520 that extend posterior from a body 521 of the vertebrae. A transverse process 530 is connected to each of the pedicels 520 and extends laterally and posteriorly outward.

Electrical lead 80 is implanted percutaneously within the epidural space 540. Electrical lead 80 can be implanted using a 14 gauge, 6 inch long Touhy needle with local anesthesia. Electrical lead 80 is placed such that electrodes 90 are proximate vertebrae T8, T9 and T10 and spinal cord 14. Electrodes 90 can enter the contralateral side to the painful side from a paramedian approach and be located an anterior side of spinal cord 14 within epidural space 540. Electrodes 90 can cross axis 550 at vertebrae T8 or T9. Approximately one half of the lead can be to the left of axis 550 and the other half to the right of axis 550.

The distal end 84 can be located at the tip of vertebrae T8. Electrical lead 80 exits the epidural space 540 between vertebrae T11 and T12 and extends through subcutaneous tissue to implantable device 40. While one electrical lead 80 is shown, more than one electrical lead may be placed proximate spinal cord 14.

Electrical lead 100 is implanted subcutaneously within the subcutaneous tissue. Electrical lead 100 is placed such that electrodes 110 are located approximately 1.5 inches laterally to the left of spinal axis 550. While shown proximate vertebrae T11 and T12, electrodes 110 can be located proximate any of the thoracic vertebrae depending upon the location of the kyphosis and/or pain experienced by the patient. Electrodes 110 can be substantially parallel to spinal cord 14 or spinal cord axis 550. The distal end 104 can be located lateral from the transverse process 530 of vertebrae T12. Electrical lead 100 extends through subcutaneous tissue to implantable device 40.

Electrical lead 120 is implanted subcutaneously within the subcutaneous tissue. Electrical lead 120 is placed such that electrodes 130 are located approximately 1.5 inches laterally to the right of spinal axis 550. While shown proximate vertebrae T11 and T12, electrodes 130 can be located proximate any of the thoracic vertebrae depending upon the location of the kyphosis and/or pain experienced by the patient. Electrodes 130 can be substantially parallel to spinal cord 14 or spinal cord axis 550. The distal end 124 can be located lateral from the transverse process 530 of vertebrae T12. Electrical lead 120 extends through subcutaneous tissue across vertebrae column 505 to implantable device 40.

Electrical leads 100 and 120 can be implanted using the same technique previously described with reference to FIG. 5. Implantable device 40 can be implanted or placed within a subcutaneous pocket 28 that is formed to receive implantable device 40. Subcutaneous pocket 28 can be located in a variety of locations and is usually located away from the location of the electrodes. Subcutaneous pocket can be located in an area such as the buttocks, abdomen or chest.

Electrodes 90, 110 and 130 can be used to deliver triangular stimulation for treating degenerative scoliosis, kyphosis and other painful conditions of the thoracic spinal region. Other types of stimulation can be delivered by electrodes 90, 110 and 130.

Figure 13:
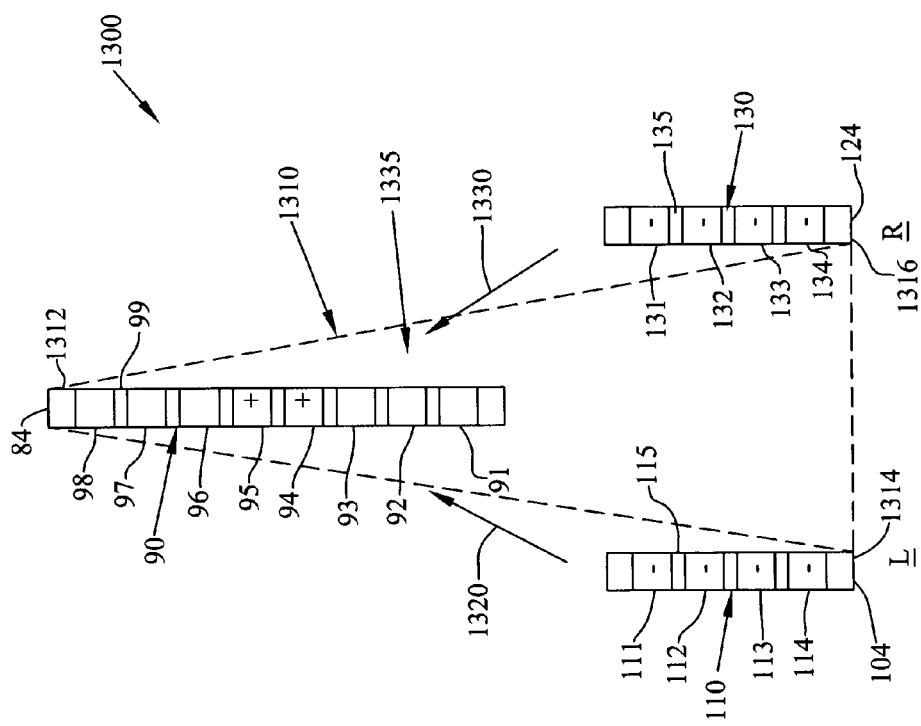
FIG. 13 is a diagram of electrode polarities representing triangular stimulation for treating degenerative scoliosis or kyphosis.

Turning now to FIG. 13, a diagram of electrode polarities representing a triangular stimulation program or triangular stimulation (TS) 1300 for treating degenerative scoliosis or kyphosis is shown. In FIG. 13, only the electrode portions of electrical leads 80, 100 and 120 (FIG. 12) are shown. The electrode combination shown in FIG. 13 can make up one electrode combination of a stimulation program for treating painful thoracic spinal conditions.

TS 1300 can include a group of electrodes 90 that are implanted proximate a spinal cord and a group of electrodes 110 and 130 that are implanted in subcutaneous tissue in a thoracic region of the back. Electrodes 110 are located on a left side (L) of an axis defined by the spinal cord when viewed from a posterior viewpoint. Electrodes 130 are located on a right side (R) of an axis defined by the spinal cord when viewed from a posterior viewpoint.

Electrodes 90, 110 and 130 are implanted to form a generally triangular shape or triangle 1310. Electrode 90 is located at one apex 1312, electrode 110 is located at one apex 1314 and electrode 130 is located at one apex 1316 of triangular shape 1310. Triangular shape 1310 can take several different types of triangular or polygon shapes. In an embodiment, the placement of electrodes 90, 110 and 130 may form the shape of an equilateral triangle between them with a relatively constant distance between each of the electrodes.

In another embodiment, the placement of electrodes 90, 110 and 130 may form the shape of an isosceles triangle between them with a relatively longer distance from electrode 90 to electrodes 110 and 130. Other triangular shapes may also be formed by electrodes 90, 110 and 130 such as scalene or obtuse. While three groups of electrodes are shown for TS 1300, more electrodes groups may be used.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 12) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 94 and 95 are both defined as anodes. Electrodes 91-93 and 96-98 are neutral. Other electrodes could be defined as anodes in electrode 90. In an embodiment, more electrodes 90 could be designated as anodes. For example, all of electrodes 91-98 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 12) through electrical leads 100 and 120 respectively.

The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as cathodes. Fewer electrodes could be defined as cathodes in electrodes 110 and 130.

Triangular stimulation 1300 causes an electrical signal with current and voltage to flow from the subcutaneous electrodes 110 and 130 proximate the thoracic region to electrodes 90 proximate the spinal cord. An electrical signal 1320 with current and voltage is induced to flow from electrodes 110 to electrodes 90. An electrical signal 1330 with current and voltage is induced to flow from electrodes 130 to electrodes 90. Electrical signals 1320 and 1330 can create a zone or field of electrical energy 1335 about the painful thoracic region. In triangular stimulation 1300, the subcutaneous electrodes 110 and 130 proximate the thoracic region communicate with electrodes 90 proximate the spinal cord. The electrical communication between electrodes 90, 110 and 130 can provide effective treatment for degenerative scoliosis and kyphosis.

The communication between the electrodes may be through nerve fibers and nerve cells in an orthodromic or antidromic manner. An orthodromic impulse runs along an axon in its normal direction, away from the soma. An antidromic impulse runs along an axon in an opposite direction, toward the soma. An antidromic impulse in an axon refers to conduction opposite to the normal, orthodromic direction.

In one embodiment, electrical signals 1320 and 1330 may deliver triangular stimulation and may have a frequency of 20 Hertz, a pulse width of 240 micro-seconds and an amplitude of 2.2 volts. Electrical signals 1320 and 1330 may have a frequency range of 5 to 100 Hertz, a pulse width range of 10 to 1000 micro-seconds and an amplitude range of 0.1 to 10.5 volts. Other frequencies, pulse widths and amplitudes can be used.

TS 1300 stimulates nerves or neural tissue in the thoracic region and blocks pain signals that originate in the thoracic region. TS 1300 can induce "parathesia", which is a sensation of numbness or tingling in the painful regions to block the transmission of pain sensations to the brain. TS 1300 can provide superior pain relief for degenerative scoliosis and kyphosis.

In one embodiment, triangular stimulation program or triangular stimulation 1300 may run concurrently with spinal cord stimulation program or spinal cord stimulation 750 (FIG. 7B). In another embodiment, triangular stimulation program or triangular stimulation 1300 may be interleaved or alternated with spinal cord stimulation program or spinal cord stimulation 750. In one other embodiment, triangular stimulation program or triangular stimulation 1300 may be run separately from spinal cord stimulation program or spinal cord stimulation 750. In another embodiment, triangular stimulation 1300 may be run with concurrently or separately with SCS and/or another PSFS program.

Figure 14:
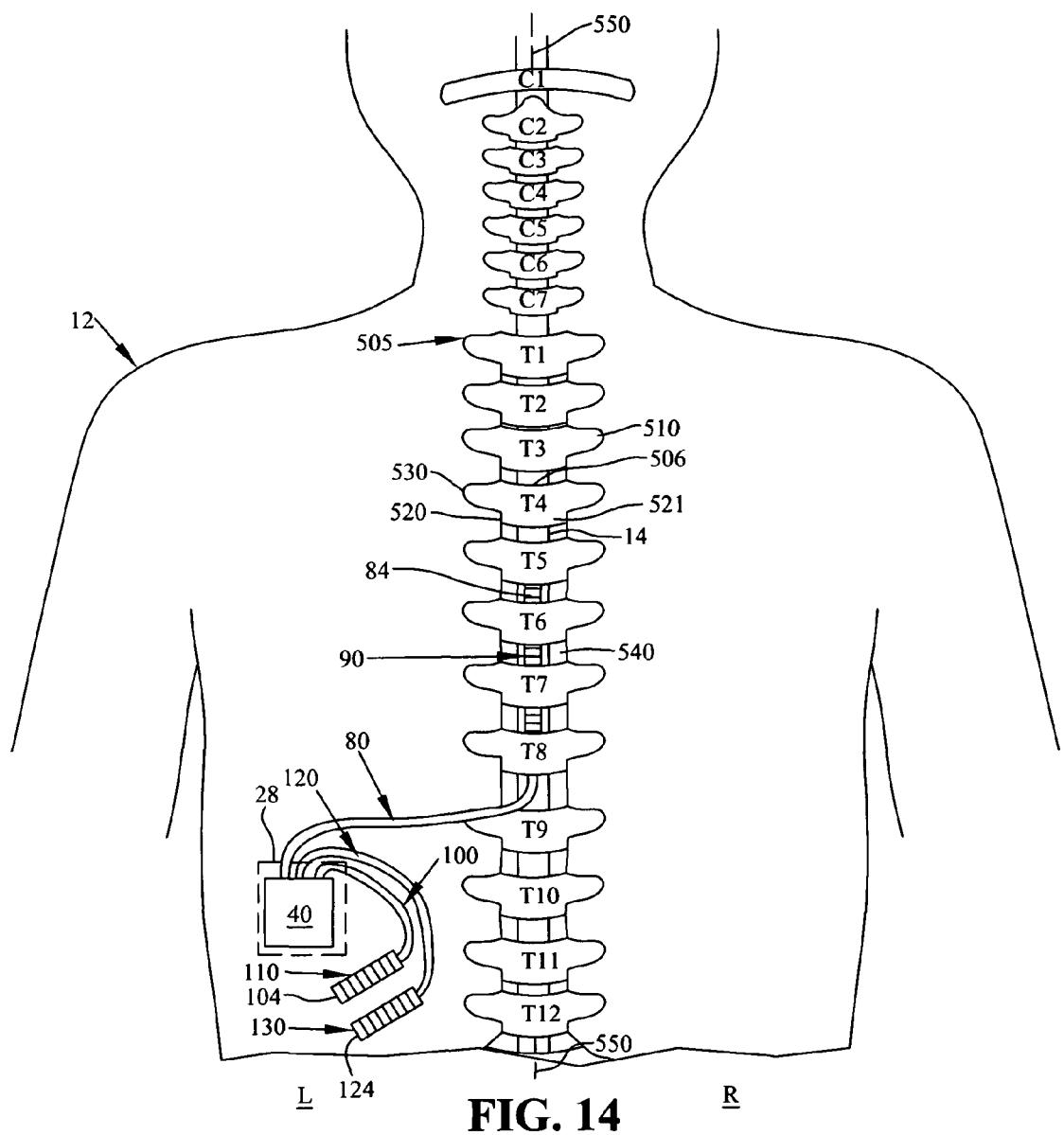
FIG. 14 is a detailed diagram of an electrical lead implanted in an epidural space in a thoracic region and pair of subcutaneous electrical leads implanted in subcutaneous tissue in a thoracic region showing the specific anatomical placement of the electrical leads in an embodiment.

FIG. 14 illustrates another anatomical placement of electrical leads for triangular stimulation in a thoracic region of a patient. In one embodiment, the electrical leads in FIG. 14 can be used to treat painful conditions such as intercostal neuralgia, chest pain or heart pain. A posterior view of patent 12 is shown in FIG. 14. Patient 12 has a vertebrae column 505 that contains individual vertebrae 510. The vertebrae shown include the thoracic vertebrae T1, T2, T3, T4, T5, T6, T7, T8, T9, T10, T11 and T12 (T1-T12) and the cervical vertebrae C1, C2, C3, C4, C5, C6 and C7 (C1-C7). The discs that are located between the vertebrae are omitted in FIG. 14 in order to show additional detail.

Spinal cord 14 extends lengthwise through the vertebrae column 505. Spinal cord 14 can have a midline or spinal axis 550 that is parallel with vertebrae column 505. Axis 550 can divide the body of patient 12 into a left half L and a right half R. Each vertebra has a vertebral foramen 506. The spinal cord 14 extends through each vertebral foramen 506. An epidural space 540 surrounds the spinal cord 14.

Each vertebra T1-T12 and L1-L5 has a pair of lateral pedicels 520 that extend posterior from a body 521 of the vertebrae. A transverse process 530 is connected to each of the pedicels 520 and extends laterally and posteriorly outward.

Electrical lead 80 is implanted percutaneously within the epidural space 540. Electrical lead 80 can be implanted using a 14 gauge, 6 inch long Touhy needle with local anesthesia. Electrical lead 80 is placed such that electrodes 90 are proximate vertebrae T6, T7 and T8 and spinal cord 14. Electrodes 90 can be located toward the painful side (left in FIG. 14) of spinal cord 14 within epidural space 540. The distal end 84 can be located at the tip of vertebrae T6. Electrical lead 80 exits the epidural space 540 between vertebrae T8 and T9 and extends through subcutaneous tissue to implantable device 40. While one electrical lead 80 is shown, more than one electrical lead may be placed proximate spinal cord 14.

Electrical lead 100 is implanted subcutaneously within the subcutaneous tissue. Electrical lead 100 is placed such that electrodes 110 are located approximately 2.0 inches laterally to the left of spinal axis 550. While shown proximate vertebrae T11 and T12, electrodes 110 can be located proximate any of the thoracic vertebrae depending upon the location of the intercostal neuralgia and/or pain experienced by the patient. Electrodes 110 can be oriented at an angle to spinal cord 14 or spinal axis 550. The angle may vary. In an embodiment, the angle may vary between 20 and 80 degrees from the spinal axis. Electrical lead 100 extends through subcutaneous tissue to implantable device 40.

Electrical lead 120 is implanted subcutaneously within the subcutaneous tissue. Electrical lead 120 is placed such that electrodes 130 are located approximately 2.0 inches laterally to the left of spinal axis 550. While shown proximate vertebrae T11 and T12, electrodes 130 can be located proximate any of the thoracic vertebrae depending upon the location of the intercostal neuralgia and/or pain experienced by the patient. Electrodes 130 can be oriented at an angle to spinal cord 14 or spinal axis 550. The angle may vary. In an embodiment, the angle may vary between 20 and 80 degrees from the spinal axis. Electrical lead 120 extends through subcutaneous tissue to implantable device 40.

Electrodes 110 and 130 are both located on the same side of the spinal axis 550. Electrical leads 100 and 120 can be implanted using the same technique previously described in FIG. 5. Implantable device 40 can be implanted or placed within a subcutaneous pocket 28 that is formed to receive implantable device 40. Subcutaneous pocket 28 can be located in a variety of locations and is usually located away from the location of the electrodes. Subcutaneous pocket can be located in an area such as the buttocks, abdomen or chest.

Electrodes 90, 110 and 130 can be used to deliver triangular stimulation for treating intercostal neuralgia, chest pain, heart pain and other painful conditions innervated by the thoracic spinal region. Other types of stimulation can be delivered by electrodes 90, 110 and 130.

Figure 15:
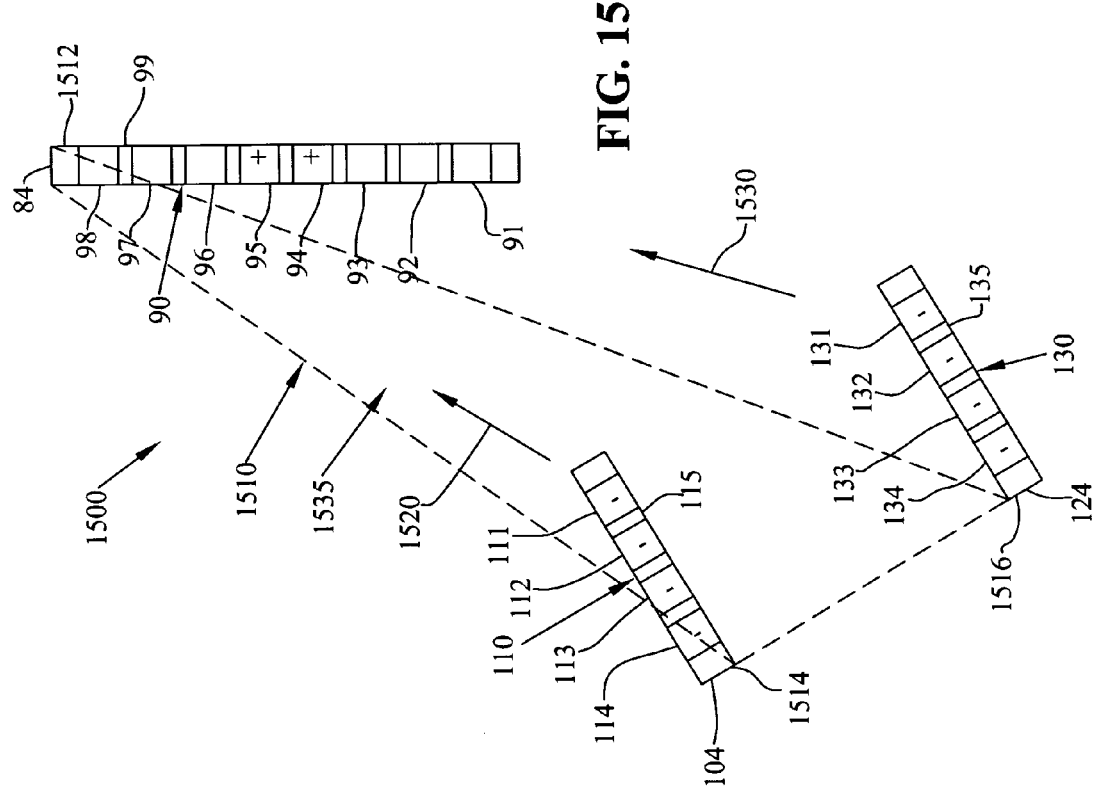
FIG. 15 is a diagram of electrode polarities representing triangular stimulation for treating intercostal neuralgia.

With reference to FIG. 15, a diagram of electrode polarities representing a triangular stimulation program or triangular stimulation (TS) 1500 for treating intercostal neuralgia, chest pain and heart pain is shown. In FIG. 15, only the electrode portions of electrical leads 80, 100 and 120 (FIG. 14) are shown. The electrode combination shown in FIG. 15 can make up one electrode combination of a stimulation program for treating painful conditions.

TS 1500 can include a group of electrodes 90 that are implanted proximate a spinal cord and a group of electrodes 110 and 130 that are implanted in subcutaneous tissue in a thoracic region of the back. Electrodes 110 and 130 are located on a left side of an axis defined by the spinal cord when viewed from a posterior viewpoint.

Electrodes 90, 110 and 130 are implanted to form a generally triangular shape or triangle 1510. Electrode 90 is located at one apex 1512, electrode 110 is located at one apex 1514 and electrode 130 is located at one apex 1516 of triangular shape 1510. Triangular shape 1510 can take several different types of triangular shapes. In an embodiment, the placement of electrodes 90, 110 and 130 may form the shape of a scalene triangle with an unequal distance between each of the electrodes. Other triangular shapes may also be formed by electrodes 90, 110 and 130. While three groups of electrodes are shown for TS 1500, more electrodes groups may be used.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 14) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 94 and 95 are both defined as anodes. Electrodes 91-93 and 96-98 are neutral. Other electrodes could be defined as anodes in electrode 90. In an embodiment, more electrodes 90 could be designated as anodes. For example, all of electrodes 91-98 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 14) through electrical leads 100 and 120 respectively.

The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as cathodes. Fewer electrodes could be defined as cathodes in electrodes 110 and 130.

Triangular stimulation 1500 causes an electrical signal with current and voltage to flow from the subcutaneous electrodes 110 and 130 proximate the thoracic region to electrodes 90 proximate the spinal cord. An electrical signal 1520 with current and voltage is induced to flow from electrodes 110 to electrodes 90. An electrical signal 1530 with current and voltage is induced to flow from electrodes 130 to electrodes 90. Electrical signals 1520 and 1530 can create a zone or field of electrical energy 1535 about the thoracic region. In triangular stimulation 1500, the subcutaneous electrodes 110 and 130 proximate the thoracic region communicate with electrodes 90 proximate the spinal cord. The electrical communication between electrodes 90, 110 and 130 can provide effective treatment for intercostal neuralgia, chest pain and heart pain.

In one embodiment, electrical signals 1520 and 1530 may deliver triangular stimulation and may have a frequency of 20 Hertz, a pulse width of 240 micro-seconds and an amplitude of 2.2 volts. Electrical signals 1520 and 1530 may have a frequency range of 5 to 100 Hertz, a pulse width range of 10 to 1000 micro-seconds and an amplitude range of 0.1 to 10.5 volts. Other frequencies, pulse widths and amplitudes can be used.

TS 1500 stimulates nerves or neural tissue in the thoracic region and blocks pain signals that originate or are innervated by the thoracic region. TS 1500 can induce "parathesia", which is a sensation of numbness or tingling in the painful regions to block the transmission of pain sensations to the brain. TS 1500 can provide pain relief from intercostal neuralgia, chest pain and heart pain.

In one embodiment, triangular stimulation program or triangular stimulation 1500 may run concurrently with spinal cord stimulation program or spinal cord stimulation 750 (FIG. 7B). In another embodiment, triangular stimulation program or triangular stimulation 1500 may be interleaved or alternated with spinal cord stimulation program or spinal cord stimulation 750. In one other embodiment, triangular stimulation program or triangular stimulation 1500 may be run separately from spinal cord stimulation program or spinal cord stimulation 750. In another embodiment, triangular stimulation 1500 may be run with concurrently or separately with SCS and/or another PSFS program.

Figure 16:
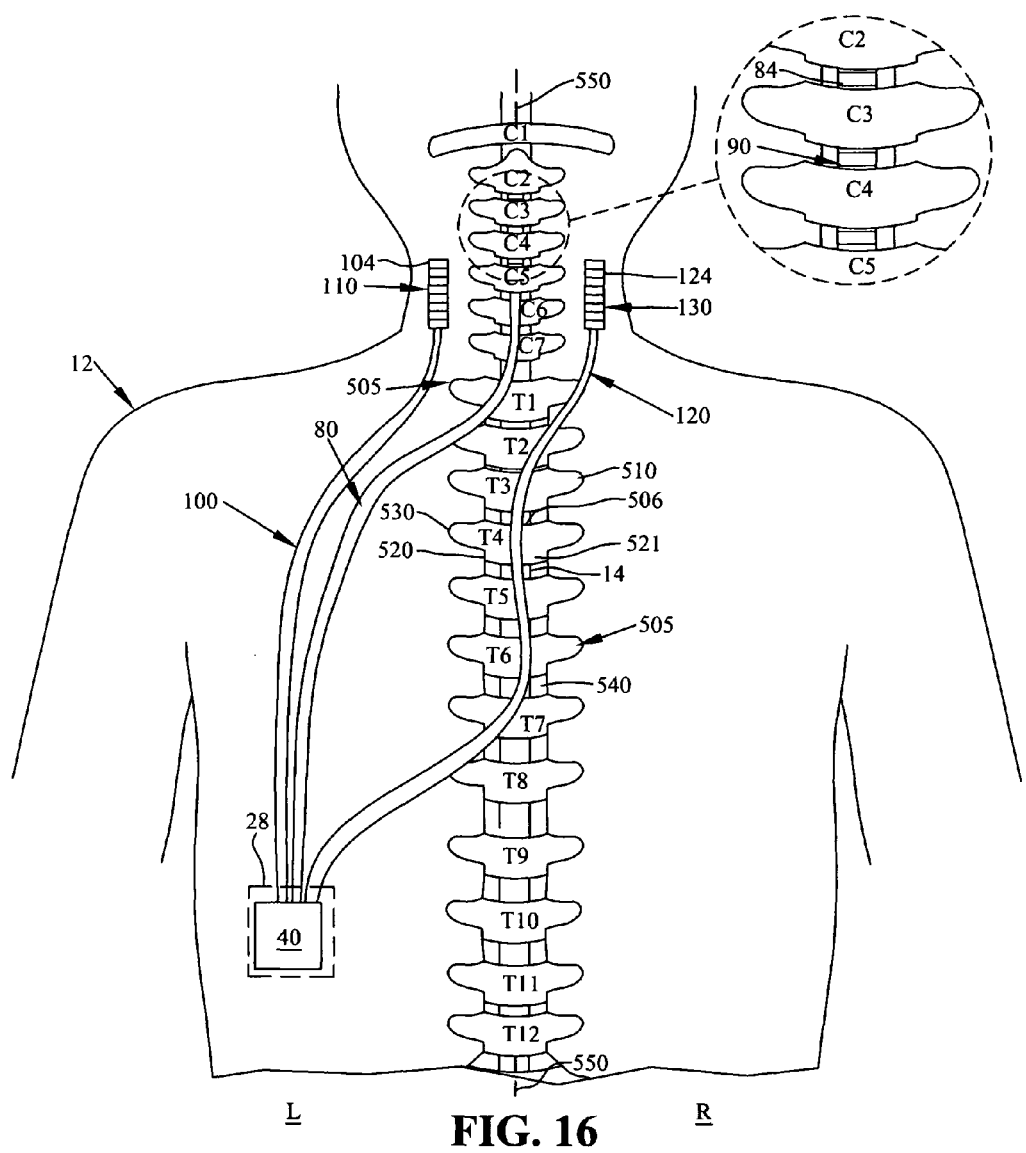
FIG. 16 is a detailed diagram of an electrical lead implanted in an epidural space in a cervical region and pair of subcutaneous electrical leads implanted in subcutaneous tissue in a cervical region showing the specific anatomical placement of the electrical leads in an embodiment.

FIG. 16 illustrates the anatomical placement of electrical leads for triangular stimulation in a cervical region of a patient. In one embodiment, the electrical leads in FIG. 16 can be used to treat neck and bi-lateral arm pain. A posterior view of patent 12 is shown in FIG. 16. Patient 12 has a vertebrae column 505 that contains individual vertebrae 510. The vertebrae shown include the thoracic vertebrae T1, T2, T3, T4, T5, T6, T7, T8, T9 and T10 (T11-T10), and the cervical vertebrae C1, C2, C3, C4, C5, C6 and C7 (C1-C7). The discs that are located between the vertebrae are omitted in FIG. 16 in order to show additional detail.

Spinal cord 14 extends lengthwise through the vertebrae column 505. Spinal cord 14 can have a midline or spinal axis 550 that is parallel with vertebrae column 505. Axis 550 can divide the body of patient 12 into a left half L and a right half R. Each vertebra has a vertebral foramen 506. The spinal cord 14 extends through each vertebral foramen 506. An epidural space 540 surrounds the spinal cord 14.

Each vertebra T1-T12 and C1-C7 has a pair of lateral pedicels 520 that extend posterior from a body 521 of the vertebrae. A transverse process 530 is connected to each of the pedicels 520 and extends laterally and posteriorly outward.

Electrical lead 80 is implanted percutaneously within the epidural space 540. Electrical lead 80 can be implanted using a 14 gauge, 6 inch long Touhy needle with local anesthesia. Electrical lead 80 is placed such that electrodes 90 are proximate vertebrae C3, C4 and C5 and spinal cord 14. Electrodes 90 can be located toward an anterior side of spinal cord 14 within epidural space 540.

The distal end 84 can be located at the tip of vertebrae C2. Electrical lead 80 exits the epidural space 540 between vertebrae C5 and C6 and extends through subcutaneous tissue to implantable device 40. While one electrical lead 80 is shown, more than one electrical lead may be placed proximate spinal cord 14.

Electrical lead 100 is implanted subcutaneously within the subcutaneous tissue. Electrical lead 100 is placed such that electrodes 110 are located approximately 1.5 inches laterally from spinal axis 550. While shown proximate vertebrae C4 and C5 near the occiput and base of the skull, electrodes 110 can be located proximate any of the cervical vertebrae depending upon the location of the neck and arm pain experienced by the patient. Electrodes 110 can be substantially parallel to spinal cord 14 or spinal cord axis 550. The distal end 104 can be located lateral from the transverse process 530 of vertebrae C3. Electrical lead 100 extends through subcutaneous tissue and is connected with implantable device 40.

Electrical lead 120 is implanted subcutaneously within the subcutaneous tissue. Electrical lead 120 is placed such that electrodes 130 are located approximately 1.5 inches laterally from spinal axis 550. While shown proximate vertebrae C4 and C5 near the occiput and base of the skull, electrodes 130 can be located proximate any of the cervical vertebrae depending upon the location of the neck and arm pain experienced by the patient. Electrodes 130 can be substantially parallel to spinal cord 14 or spinal cord axis 550. The distal end 124 can be located lateral from the transverse process 530 of vertebrae C3. Electrical lead 120 extends through subcutaneous tissue across vertebrae column 505 and is connected with implantable device 40.

Electrical leads 100 and 120 can be implanted using the same technique previously described with regards to FIG. 5. Implantable device 40 can be implanted or placed within a subcutaneous pocket 28 that is formed to receive implantable device 40. Subcutaneous pocket 28 can be located in a variety of locations and is usually located away from the location of the electrodes. Subcutaneous pocket can be located in an area such as the buttocks, abdomen or chest.

Electrodes 90, 110 and 130 can be used to deliver triangular stimulation for treating neck and bi-lateral arm pain and other painful conditions of the cervical spinal region. Other types of stimulation can be delivered by electrodes 90, 110 and 130.

Figure 17:
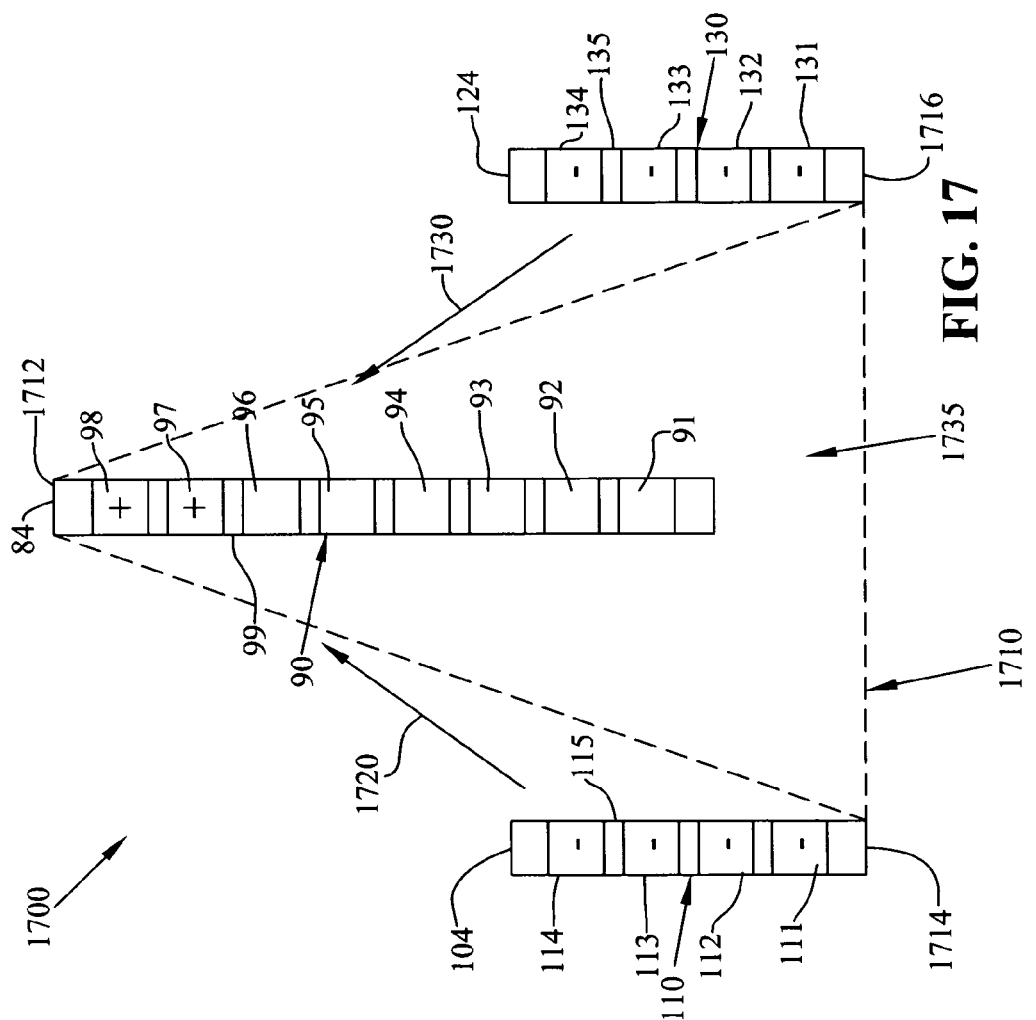
FIG. 17 is a diagram of electrode polarities representing triangular stimulation for treating neck pain and bilateral arm pain.

Turning now to FIG. 17, a diagram of electrode polarities representing a triangular stimulation program or triangular stimulation (TS) 1700 for treating neck and arm pain is shown. In FIG. 17, only the electrode portions of electrical leads 80, 100 and 120 (FIG. 16) are shown. The electrode combination shown in FIG. 17 can make up one electrode combination of a stimulation program for treating painful cervical spinal conditions.

TS 1700 can include a group of electrodes 90 that are implanted proximate a spinal cord in a cervical region and a group of electrodes 110 and 130 that are implanted in subcutaneous tissue in a cervical region of the back. Electrodes 110 are located on a left side of an axis defined by the spinal cord when viewed from a posterior viewpoint. Electrodes 130 are located on a right side of an axis defined by the spinal cord when viewed from a posterior viewpoint.

Electrodes 90, 110 and 130 are implanted to form a generally triangular shaped area or triangle 1710. Electrode 90 is located at one apex 1712, electrode 110 is located at one apex 1714 and electrode 130 is located at one apex 1716 of triangular shape 1510. Triangular shape 1710 can take several different types of triangular shapes. In an embodiment, the placement of electrodes 90, 110 and 130 may form the shape of a scalene or obtuse triangle with an unequal distance between each of the electrodes. Other triangular shapes may also be formed by electrodes 90, 110 and 130. While three groups of electrodes are shown for TS 1700, more electrodes groups may be used. It is noted that in FIGS. 16 and 17 that a portion of electrodes 110 and 130 are aligned to overlap with a portion of electrodes 90 when moving perpendicularly away from electrodes 90.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 16) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 98 and 97 are both defined as anodes. Electrodes 91-96 are neutral. Other electrodes could be defined as anodes in electrode 90. In an embodiment, more electrodes 90 could be designated as anodes. For example, all of electrodes 91-98 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 16) through electrical leads 100 and 120 respectively.

The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as cathodes. Fewer electrodes could be defined as cathodes in electrodes 110 and 130.

Triangular stimulation 1700 causes an electrical signal with current and voltage to flow from the subcutaneous electrodes 110 and 130 proximate the cervical region to electrodes 90 proximate the spinal cord. An electrical signal 1720 with current and voltage is induced to flow from electrodes 110 to electrodes 90. An electrical signal 1730 with current and voltage is induced to flow from electrodes 130 to electrodes 90. Electrical signals 1720 and 1730 can create a zone or field of electrical energy 1735 about the cervical region. In triangular stimulation 1700, the subcutaneous electrodes 110 and 130 proximate the cervical region communicate with electrodes 90 proximate the spinal cord. The electrical communication between electrodes 90, 110 and 130 can provide effective treatment for neck and arm pain.

The communication between the electrodes may be through nerve fibers and nerve cells in an orthodromic or antidromic manner. An orthodromic impulse runs along an axon in its normal direction, away from the soma. An antidromic impulse runs along an axon in an opposite direction, toward the soma. An antidromic impulse in an axon refers to conduction opposite to the normal, orthodromic direction.

In one embodiment, electrical signals 1720 and 1730 may deliver triangular stimulation and may have a frequency of 20 Hertz, a pulse width of 240 micro-seconds and an amplitude of 2.2 volts. Electrical signals 1720 and 1730 may have a frequency range of 5 to 100 Hertz, a pulse width range of 10 to 1000 micro-seconds and an amplitude range of 0.1 to 10.5 volts. Other frequencies, pulse widths and amplitudes can be used.

TS 1700 stimulates nerves or neural tissue in the cervical region and blocks pain signals that originate in the cervical region. TS 1700 can induce "parathesia", which is a sensation of numbness or tingling in the painful regions to block the transmission of pain sensations to the brain. TS 1700 can provide pain relief for neck and arm pain In one embodiment, triangular stimulation program or triangular stimulation 1700 may run concurrently with spinal cord stimulation program or spinal cord stimulation 750 (FIG. 7B). In another embodiment, triangular stimulation program or triangular stimulation 1700 may be interleaved or alternated with spinal cord stimulation program or spinal cord stimulation 750. In one other embodiment, triangular stimulation program or triangular stimulation 1700 may be run separately from spinal cord stimulation program or spinal cord stimulation 750. In another embodiment, triangular stimulation 1700 may be run with concurrently or separately with SCS and/or another PSFS program.

Figure 18:
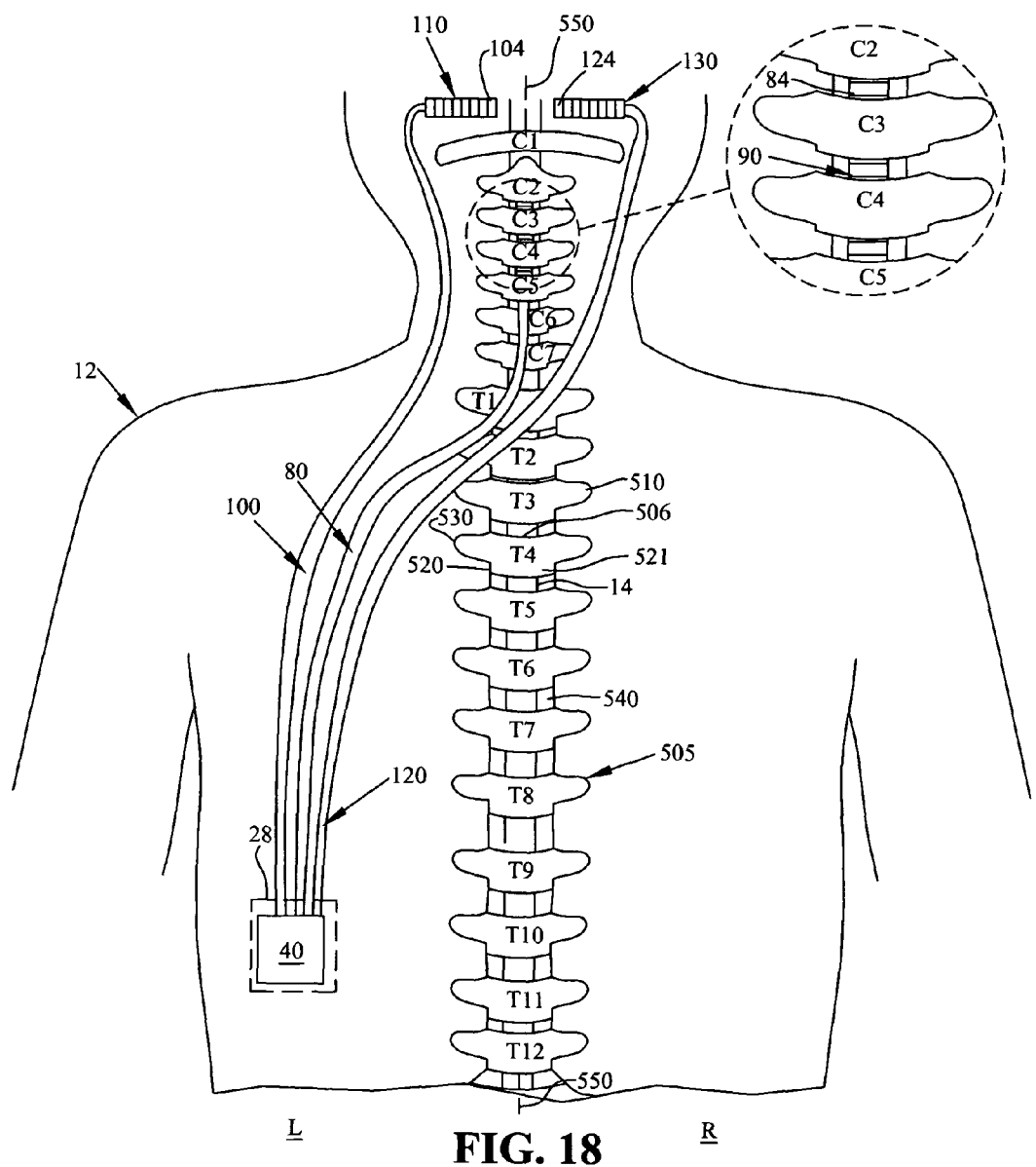
FIG. 18 is a detailed diagram of an electrical lead implanted in an epidural space in a cervical region and pair of subcutaneous electrical leads implanted in subcutaneous tissue in an occipital region showing the specific anatomical placement of the electrical leads in an embodiment.

With reference to FIG. 18, the anatomical placement of electrical leads for triangular stimulation in an occipital region of a patient is illustrated. In one embodiment, the electrical leads in FIG. 18 can be used to treat occipital nerve pain, occipital neuralgia and occipital headache. A posterior view of patent 12 is shown in FIG. 18. Patient 12 has a vertebrae column 505 that contains individual vertebrae 510. The vertebrae shown include the thoracic vertebrae T1, T2, T3, T4, T5, T6, T7, T8 and T9 (T1-T9) and the cervical vertebrae C1, C2, C3, C4, C5, C6 and C7 (C1-C7). The discs that are located between the vertebrae are omitted in FIG. 18 in order to show additional detail.

Spinal cord 14 extends lengthwise through the vertebrae column 505. Spinal cord 14 can have a midline or spinal axis 550 that is parallel with vertebrae column 505. Axis 550 can divide the body of patient 12 into a left half L and a right half R. Each vertebra has a vertebral foramen 506. The spinal cord 14 extends through each vertebral foramen 506. An epidural space 540 surrounds the spinal cord 14.

Each vertebra T1-T12 and C1-C7 has a pair of lateral pedicels 520 that extend posterior from a body 521 of the vertebrae. A transverse process 530 is connected to each of the pedicels 520 and extends laterally and posteriorly outward.

Electrical lead 80 is implanted percutaneously within the epidural space 540. Electrical lead 80 can be implanted using a 14 gauge, 6 inch long Touhy needle with local anesthesia. Electrical lead 80 is placed such that electrodes 90 are proximate vertebrae C3, C4 and C5 and spinal cord 14. Electrodes 90 can be located toward an anterior side of spinal cord 14 within epidural space 540.

The distal end 84 can be located at the tip of vertebrae C3. Electrical lead 80 exits the epidural space 540 between vertebrae C5 and C6 and extends through subcutaneous tissue to implantable device 40. While one electrical lead 80 is shown, more than one electrical lead may be placed proximate spinal cord 14.

Electrical lead 100 is implanted subcutaneously within the subcutaneous tissue. Electrical lead 100 is placed such that electrodes 110 are located to the left of the spinal axis 550 and approximately over to slightly above vertebrae C1. Electrodes 110 can be oriented substantially perpendicular to spinal cord 14 or spinal cord axis 550. Electrodes 110 may be placed over the greater occipital nerve, the lesser occipital nerve or may extend over both the greater and less occipital nerves.

Electrodes 110 can be located either above or below vertebrae C1 depending upon the location of the occipital pain experienced by the patient. The distal end 104 can be located toward spinal cord 14 or may be oriented away from spinal cord 14. Electrical lead 100 extends through subcutaneous tissue and is connected with implantable device 40.

Electrical lead 120 is implanted subcutaneously within the subcutaneous tissue. Electrical lead 120 is placed such that electrodes 130 are located to the right of the spinal axis 550 and approximately over to slightly above vertebrae C1. Electrodes 130 can be oriented substantially perpendicular to spinal cord 14 or spinal cord axis 550. Electrodes 130 may be placed over the greater occipital nerve, the lesser occipital nerve or may extend over both the greater and less occipital nerves.

Electrodes 130 can be located either above or below vertebrae C 1 depending upon the location of the occipital pain experienced by the patient. The distal end 124 can be located toward spinal cord 14 or may be oriented away from spinal cord 14. Electrical lead 120 extends through subcutaneous tissue and is connected with implantable device 40.

Electrical leads 100 and 120 can be implanted using the same technique previously described with regards to FIG. 5. Implantable device 40 can be implanted or placed within a subcutaneous pocket 28 that is formed to receive implantable device 40. Subcutaneous pocket 28 can be located in a variety of locations and is usually located away from the location of the electrodes. Subcutaneous pocket can be located in an area such as the buttocks, abdomen or chest.

Electrodes 90, 110 and 130 can be used to deliver triangular stimulation for treating occipital nerve pain, occipital neuralgia and occipital headache. Other types of stimulation can be delivered by electrodes 90, 110 and 130.

Figure 19:
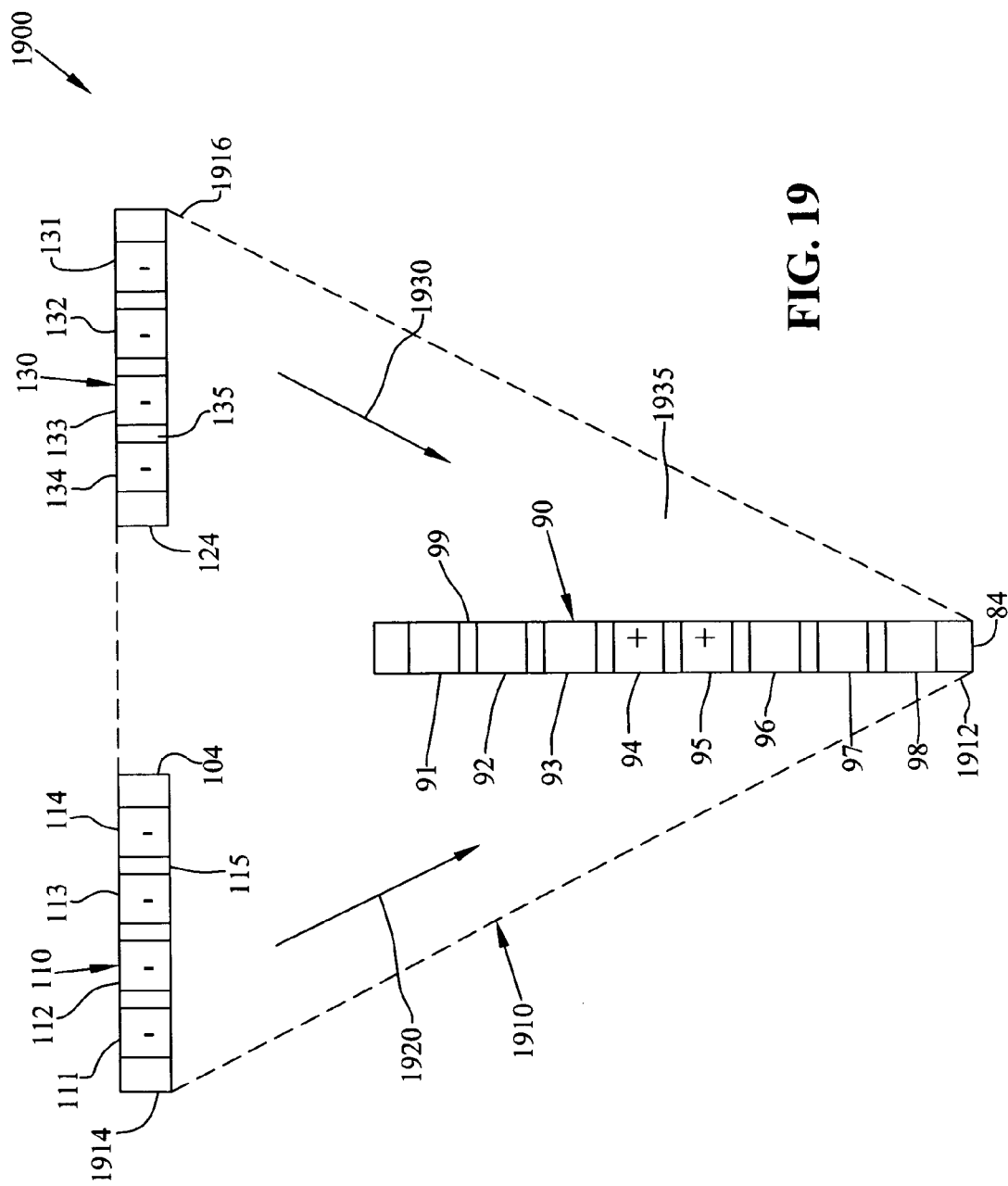
FIG. 19 is a diagram of electrode polarities representing triangular stimulation for treating occipital neuralgia.

Turning now to FIG. 19, a diagram of electrode polarities representing a triangular stimulation program or triangular stimulation (TS) 1900 for treating occipital nerve pain, occipital neuralgia and occipital headache. In FIG. 19, only the electrode portions of electrical leads 80, 100 and 120 (FIG. 18) are shown. The electrode combination shown in FIG. 19 can make up one electrode combination of a stimulation program for treating painful occipital nerve conditions.

TS 1900 can include a group of electrodes 90 that are implanted proximate a spinal cord and a group of electrodes 110 and 130 that are implanted in subcutaneous tissue in a cervical, neck or back of the head region. Electrodes 110 are located on a left side of an axis defined by the spinal cord when viewed from a posterior viewpoint. Electrodes 130 are located on a right side of an axis defined by the spinal cord when viewed from a posterior viewpoint.

Electrodes 90, 110 and 130 are implanted to form a generally inverted triangular shape or triangle 1910. Electrode 90 is located at one apex 1912, electrode 110 is located at one apex 1914 and electrode 130 is located at one apex 1916 of triangular shape 1910. Triangular shape 1910 can take several different types of triangular or polygon shapes. In an embodiment, the placement of electrodes 90, 110 and 130 may form the shape of a equilateral triangle with equal distances between each of the electrodes. Other triangular shapes may also be formed by electrodes 90, 110 and 130. While three groups of electrodes are shown for TS 1900, more electrodes groups may be used.

Electrodes 90 have a generally elongated cylindrical shape and include eight circumferential electrodes that are separated by a region of insulation 99. Electrodes 90 include individual electrodes 91, 92, 93, 94, 95, 96, 97 and 98. Each of electrodes 91-98 is electrically connected to implantable device 40 (FIG. 18) through electrical lead 80. The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 94 and 95 are both defined as anodes. Electrodes 91-93 and 96-98 are neutral. Other electrodes could be defined as anodes in electrode 90. In an embodiment, more electrodes 90 could be designated as anodes. For example, all of electrodes 91-98 may be programmed as anodes in one embodiment.

Electrodes 110 and 130 also have a generally elongated cylindrical shape and include four circumferential electrodes that are separated by regions of insulation 115 and 135 respectively. Electrodes 110 include individual electrodes 111, 112, 113 and 114. Electrodes 130 include individual electrodes 131, 132, 133 and 134. Each of electrodes 111-114 and 131-134 are electrically connected to implantable device 40 (FIG. 18) through electrical leads 100 and 120 respectively.

The polarity of each electrode can be controlled by the implantable device according to a stimulation program. A positive sign (+) indicates an anode while a negative sign (−) indicates a cathode and a blank space ( ) defines no polarity, neutral or no applied current or voltage. Electrodes 111, 112, 113 and 114 are defined as cathodes. Electrodes 131, 132, 133 and 134 are defined as cathodes. Fewer electrodes could be defined as cathodes in electrodes 110 and 130.

Triangular stimulation 1900 causes an electrical signal with current and voltage to flow from the subcutaneous electrodes 110 and 130 proximate the occipital nerves to electrodes 90 proximate the spinal cord. An electrical signal 1920 with current and voltage is induced to flow from electrodes 110 to electrodes 90. An electrical signal 1930 with current and voltage is induced to flow from electrodes 130 to electrodes 90. Electrical signals 1920 and 1930 can create a zone or field of electrical energy 1935 about the occipital nerves and a cervical region. In triangular stimulation 1900, the subcutaneous electrodes 110 and 130 proximate the occipital nerves communicate with electrodes 90 proximate the spinal cord. The electrical communication between electrodes 90, 110 and 130 can provide effective treatment for occipital nerve pain, occipital neuralgia and occipital headache.

In one embodiment, electrical signals 1920 and 1930 may deliver triangular stimulation and may have a frequency of 20 Hertz, a pulse width of 240 micro-seconds and amplitude of 2.2 volts. Electrical signals 1920 and 1930 may have a frequency range of 5 to 100 Hertz, a pulse width range of 10 to 1000 micro-seconds and an amplitude range of 0.1 to 10.5 volts. Other frequencies, pulse widths and amplitudes can be used. TS 1900 stimulates nerves or neural tissue in the occipital nerves and blocks pain signals that originate in the occipital nerves.

In one embodiment, triangular stimulation program or triangular stimulation 1900 may run concurrently with spinal cord stimulation program or spinal cord stimulation 750 (FIG. 7B). In another embodiment, triangular stimulation program or triangular stimulation 1900 may be interleaved or alternated with spinal cord stimulation program or spinal cord stimulation 750. In one other embodiment, triangular stimulation program or triangular stimulation 1900 may be run separately from spinal cad stimulation program or spinal cord stimulation 750. In another embodiment, triangular stimulation 1900 may be run with concurrently or separately with SCS and/or another PSFS program.

The present apparatuses, methods and systems described herein can provide a patient with pain relief through the use of several novel neurostimulation programs and electrical lead placements. Triangular stimulation provides an electrical signal that flows from subcutaneous tissue to the epidural space proximate the spinal cord. Flow stimulation provides an electrical signal that flows across an area of subcutaneous tissue proximate a painful area.

Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A system for treating pain comprising:
at least one implantable device that is configured to generate a plurality of electrical signals;
a spinal lead having a first end connected to the implantable device and a second end connected to a first set of electrodes, the first set of electrodes in communication with the implantable device and implantable within an epidural space proximate to a spinal cord;
a first subcutaneous lead having a third end connected to the implantable device and a fourth end connected to a second set of electrodes, the second set of electrodes in communication with the implantable device and implantable at least partially within subcutaneous tissue and positioned on a first side of the spinal cord;
a second subcutaneous lead having a fifth end connected to the implantable device and a sixth end connected to a third set of electrodes, the third set of electrodes in communication with the implantable device and implantable at least partially within subcutaneous tissue and positioned on a second side of the spinal cord; and
wherein the second and third sets of electrodes are spaced apart from each other on opposite sides of a spinal cord axis and the first set of electrodes are spaced along the spinal cord axis longitudinally apart from the second and third sets of electrodes to form a triangular shape, the implantable device programmed with a stimulation program that causes the electrical signals to be transmitted between the second and third sets of electrodes in the subcutaneous tissue and the first set of electrodes in the epidural space providing a field of electrical stimulation about the triangular shape.

2. The system of claim 1, wherein the first set of electrodes are configured as anodes and the second and third sets of electrodes are configured as cathodes such that a current is induced flow from the second and third sets of electrodes to the first set of electrodes within the epidural space.

3. The system of claim 1, wherein the first set of electrodes are configured as cathodes and the second and third sets of electrodes are configured as anodes such that a current is induced to flow from the first set of electrodes within the epidural space to the second and third sets of electrode.

4. The system of claim 1, wherein the first set of electrodes arc positioned within the epidural space in a thoracic region and the second and third sets of electrodes are subcutaneously positioned in a lumbar region.

5. The system of claim 1, wherein the first set of electrodes have a seventh end positioned at a first apex of the triangular shape and the second set of electrodes have an eighth end positioned at a second apex of the triangular shape and the third set of electrodes have a ninth end positioned at a third apex of the triangular shape.

6. The system of claim 1, further comprising;
programming the implantable device with a triangular stimulation program;
testing the triangular stimulation program; and
setting the triangular stimulation program as a permanent program.

7. new The system of claim 1, further comprising:
determining if pain covers a broad area or a focal area;
in response to pain covering the focal area, programming the implantable device with a flow stimulation program; and
in response to pain covering the broad area, programming the implantable device with a peripheral subcutaneous field stimulation program.

8. An apparatus for treating pain comprising;
a first set of spinal electrodes connected to a first electrical lead, the first electrical lead having a first end and a second end, the second end connected to the first set of spinal electrodes, the first set of spinal electrodes configured to be implanted within an epidural space proximate to a spinal cord;
a second set of subcutaneous electrodes connected to a second electrical lead, the second electrical lead having a third end and a fourth end, the fourth end connected to the second set of subcutaneous electrodes, the second set of subcutaneous electrodes configured to be implanted at least partially within subcutaneous tissue and positioned proximate a lumbar region on a first side of the spinal cord;
a third set of subcutaneous electrodes connected to a third electrical lead, the third electrical lead having a fifth end and a sixth end, the sixth end connected to the third set of subcutaneous electrodes, the third set of subcutaneous electrodes configured to be implanted at least partially within subcutaneous tissue and positioned proximate the lumbar region on a second side of the spinal cord;
the second and third sets of subcutaneous electrodes spaced apart from each other on opposite sides of a spinal cord axis and the first set of spinal electrodes spaced along the spinal cord axis distally apart from the second and third sets of subcutaneous electrodes to form a triangular shape; and
at least one implantable device, the first end of the first electrical lead, the third end of the second electrical lead and the fifth end of the third electrical lead connected to the implantable device, the implantable device in communication with the first, second and third sets of electrodes, the implantable device having a processor in communication with a memory and an electrode driver;
software operable on. the processor to:
receive a plurality of stimulation programs;
trigger the electrode driver to generate a plurality of electrical signals based on the stimulation programs; and
trigger the electrode driver to transmit the electrical signals between the subcutaneous electrodes and the spinal electrodes to provide a field of electrical stimulation about the triangular shape.

9. The apparatus of claim 8, wherein the first set of spinal electrodes are configured us anodes and the second and third sets of subcutaneous electrodes are configured as cathodes such that a current is induced to flow from the second and third sets of subcutaneous electrodes to the first set of spinal electrodes.

10. The apparatus of claim 8, wherein the first set of spinal electrodes are configured as cathodes and the second and third sets of subcutaneous electrodes are configured as anodes such that a current is induced to flow from the first set of spinal electrodes to the second and third sets of subcutaneous electrodes.

11. The apparatus of claim 8, wherein the processor is programmed with a triangular stimulation program that causes a zone of parathesia between the first, second and third sets of electrodes.

12. The apparatus of claim 8, further comprising an external programming device in communication with the implantable device, the external programming device operable to transmit the stimulation programs to the implantable device.

13. The apparatus of claim 8, further comprising the first set of spinal electrodes having a seventh end positioned at a first apex of the triangular shape and the second set of subcutaneous electrodes having an eighth end positioned at a second apex of the triangular shape and the third set of subcutaneous electrodes having a ninth end positioned at a third apex of the triangular shape.

14. The apparatus of claim 8, further comprising:
programming the implantable device with a triangular stimulation program;
testing the triangular stimulation program; and
setting the triangular stimulation program as a permanent program.

15. The apparatus of claim 13, further comprising:
determining if ventral stimulation is present; and
in response to no ventral stimulation being present, setting the triangular stimulation program as a permanent program.

16. An apparatus for treating pain comprising:
an implantable device having a processor and a memory in communication with the processor, the memory storing one or more stimulation programs, the implantable device further having an electrode driver in communication with the processor, the electrode driver generating a plurality of electrical stimulation signals;
a first lead having a first end connected to the implantable device and a second end connected to a set of spinal electrodes, the spinal electrodes in communication with the electrode driver and configured to be implanted within an epidural space proximate to a spinal cord and positioned in a thoracic region;
a second lead having a third end connected to the implantable device and a fourth end connected to a first set of subcutaneous electrodes, the first set of subcutaneous electrodes in communication with the electrode driver and configured to be implanted at least partially within subcutaneous tissue and positioned in a lumbar region on a first side of the spinal cord; and
a third lead having a fifth end connected to ₁he implantable device and a sixth end connected to a second set of subcutaneous electrodes, the second set of subcutaneous electrodes in communication with the electrode driver and configured to be implanted at least partially within subcutaneous tissue and positioned in the lumbar region on a second side of the spinal cord;
the first and second sets of subcutaneous electrodes located in the lumbar region and spaced apart from each other on opposite sides of a spinal cord axis and the set of spinal electrodes positioned in the thoracic region and spaced longitudinally apart from the first and second sets of subcutaneous electrodes, the first and second sets of subcutaneous electrodes and the spinal electrodes forming a triangular region; and
a triangular stimulation program stored in the memory and operable on the processor, the triangular stimulation program causing the electrode driver to transmit the electrical stimulation signals between the sets of subcutaneous electrodes and the set of spinal electrodes providing electrical stimulation proximate the triangular region.

17. The apparatus of claim 16, wherein the spinal electrodes have a seventh end positioned at a first apex of the triangular region and the second set of subcutaneous electrodes have an eighth end positioned at a second apex of the triangular region and the third set of subcutaneous electrodes having a ninth end positioned at a third apex of the triangular region.

18. The apparatus of claim 16, wherein the first set of spinal electrodes are configured as anodes and the second and third sets of subcutaneous electrodes are configured as cathodes such that a current is induced to flow from the lumbar region to the thoracic region epidural space.

19. The apparatus of claim 16, further comprising:
testing the triangular stimulation program; and
setting the triangular stimulation program as a permanent program.

20. The apparatus of claim 16, further comprising an external programming device in communication with the implantable device, the external programming device operable to transmit the triangular stimulation program to the implantable device.

* * * * *